US010596247B2

(12) United States Patent
Zhong

(10) Patent No.: US 10,596,247 B2
(45) Date of Patent: Mar. 24, 2020

(54) METHODS AND COMPOSITIONS FOR ATTENUATED CHLAMYDIA AS VACCINE AND VECTOR

(71) Applicant: Board of Regents, The University of Texas System, San Antonio, TX (US)

(72) Inventor: Guangming Zhong, San Antonio, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 15/551,829

(22) PCT Filed: Feb. 19, 2016

(86) PCT No.: PCT/US2016/018746
§ 371 (c)(1),
(2) Date: Aug. 17, 2017

(87) PCT Pub. No.: WO2016/134300
PCT Pub. Date: Aug. 25, 2016

(65) Prior Publication Data
US 2018/0021423 A1    Jan. 25, 2018

Related U.S. Application Data

(60) Provisional application No. 62/118,961, filed on Feb. 20, 2015.

(51) Int. Cl.
*A01N 63/00*    (2006.01)
*A61K 48/00*    (2006.01)
*A61K 39/00*    (2006.01)
*A61K 39/118*   (2006.01)
*C12N 1/36*     (2006.01)
*C07K 14/295*   (2006.01)

(52) U.S. Cl.
CPC .......... *A61K 39/118* (2013.01); *C07K 14/295* (2013.01); *C12N 1/36* (2013.01); *A61K 2039/522* (2013.01)

(58) Field of Classification Search
CPC ....... C12N 15/86; A61K 38/00; C07K 14/295
See application file for complete search history.

(56) References Cited

U.S. PATENT DOCUMENTS

| 3,610,795 | A | 10/1971 | Antoine |
| 4,501,729 | A | 2/1985 | Boucher et al. |
| 4,708,871 | A | 11/1987 | Geysen |
| 4,968,603 | A | 11/1990 | Slamon et al. |
| 5,869,248 | A | 2/1999 | Yuan et al. |
| 5,877,022 | A | 3/1999 | Stinchcomb et al. |
| 6,013,487 | A | 1/2000 | Mitchell |
| 6,083,702 | A | 7/2000 | Mitchell et al. |
| 6,822,071 | B1 | 11/2004 | Stephens et al. |
| 7,071,172 | B2 | 7/2006 | McCown et al. |
| 7,201,898 | B2 | 4/2007 | Monahan et al. |
| 7,361,353 | B2 * | 4/2008 | Grandi ................. A61K 39/118 424/190.1 |
| 2003/0017131 | A1 | 1/2003 | Park et al. |
| 2004/0013645 | A1 | 1/2004 | Monahan et al. |
| 2004/0131625 | A1 * | 7/2004 | Berthet ................ A61K 39/118 424/184.1 |
| 2005/0281847 | A1 | 12/2005 | Berthet et al. |
| 2006/0034871 | A1 | 2/2006 | Grandi et al. |
| 2011/0256094 | A1 | 10/2011 | Zhong |
| 2013/0095487 | A1 | 4/2013 | Carter et al. |
| 2013/0171238 | A1 | 7/2013 | Grandi et al. |

FOREIGN PATENT DOCUMENTS

| WO | WO 90/05142 A1 | 5/1990 |
| WO | WO 94/00153 A1 | 1/1994 |
| WO | WO 95/17210 A1 | 6/1995 |
| WO | WO 96/33739 A1 | 10/1996 |
| WO | WO 03/049762 A2 | 6/2003 |
| WO | WO 03/095647 A2 | 11/2003 |
| WO | WO 2006/021724 A2 | 3/2006 |
| WO | WO 2006/029319 A2 | 3/2006 |
| WO | WO 2006/073052 A1 | 7/2006 |
| WO | WO 2006/119137 A1 | 11/2006 |
| WO | WO 2007/100465 A2 | 9/2007 |
| WO | WO 2008/088895 A2 | 7/2008 |

OTHER PUBLICATIONS

Thomas et al., Genome Res., 2008; 18: 161-171 (Year: 2008).*
Carlson et al., Infection and Immunity, 2005; 73(10): 6407-6418 (Year: 2005).*
Conrad et al. "The Chromosome-Encoded Hypothetical Protein TC0668 Is an Upper Genital Tract Pathogenicity Factor of Chlamydia muridarum" Infection and Immunity, 84(2):467-479 (2016).
Extended European Search Report corresponding to European Patent Application no. 16753176.3 (9 pages) (dated Jul. 19, 2018).
Shao et al. "Chlamydia muridarum with Mutations in Chromosomal Genes tc0237 and/or tc0668 Is Deficient in Colonizing the Mouse Gastrointestinal Tract" Infection and Immunity, 85(8):1-13 (2017).
Chen et al. "In Vitro Passage Selects for *Chlamydia muridarum* with Enhanced Infectivity in Cultured Cells but Attenuated Pathogenicity in Mouse Upper Genital Tract" *Infections and Immunity* 83(5):1881-1892 (2015).
International Search Report and the Written Opinion of the International Searching Authority corresponding to International Patent Application No. PCT/US2016/018746 (11 pages) (dated Jul. 21, 2016).

(Continued)

*Primary Examiner* — Gary B Nickol
*Assistant Examiner* — Lakia J Jackson-Tongue
(74) *Attorney, Agent, or Firm* — Myers Bigel, P.A.

(57) ABSTRACT

The present invention provides *Chlamydia* organisms and compositions and methods of use in the treatment/prevention of chlamydial infection in a subject, for eliciting an immune response in a subject and for use as vectors.

8 Claims, 8 Drawing Sheets
Specification includes a Sequence Listing.

(56) References Cited

OTHER PUBLICATIONS

Altschul et al. "Basic Local Alignment Search Tool" *Journal of Molecular Biology* 215(3):403-410 (1990).
Altschul et al. "Local alignment statistics" *Methods in Enzymology* 266:460-480 (1996).
Altschul et al. "Gapped BLAST and PSI-BLAST: a new generation of protein database search programs" *Nucleic Acids Research* 25(17):3389-3402 (1997).
Andino et al. "AAV-mediated knockdown of phospholamban leads to improved contractility and calcium handling in cardiomyocytes" *The Journal of Gene Medicine* 10(2):132-142 (2008).
Brichard et al. "The Tyrosinase Gene Codes for an Antigen Recognized by Autologous Cytolytic T Lymphocytes on HLA-A2 Melanomas" *The Journal of Experimental Medicine* 178(2):489-495 (1993).
Devereux et al. "A comprehensive set of sequence analysis programs for the VAX" *Nucleic Acids Research* 12(1):387-395 (1984).
GenBank Accession No. J00306 "Human somatostatin I gene and flanks" *NCBI* (2 pages) (Jan. 13, 1995).
GenBank Accession No. NC_002182 "Chlamydia muridarum Nigg Plasmid pMoPn, complete sequence" *NCBI* (5 pages) (Mar. 29, 2017).
GenBank Accession No. NC_002620 "Chlamydia muridarum Nigg, complete genome" *NCBI* (344 pages) (Mar. 29, 2017).
GenBank Accession No. P01166 "Somatostatin precursor [Contains: Somatostatin-28; Somatostatin-14]" *NCBI* (3 pages) (Sep. 15, 2003).
Geysen et al. "Use of peptide synthesis to probe viral antigens for epitopes to a resolution of a single amino acid" *Proceedings of the National Academy of Sciences* 81(13):3998-4002 (1984).
Geysen et al. "A Priori Delineation of a Peptide Which Mimics a Discontinuous Antigenic Determinant" *Molecular Immunology* 23(7):709-715 (1986).
Gorman et al. "Stable alteration of pre-mRNA splicing patterns by modified U7 small nuclear RNAs" *Proceedings of the National Academy of Sciences* 95(9):4929-4934 (1998).
Gregorevic et al. "Systemic Microdystrophin Gene Delivery Improves Skeletal Muscle Structure and Function in Old Dystrophic mdx Mice" *Molecular Therapy* 16(4):657-664 (2008).
Hopp et al. "Prediction of protein antigenic determinants from amino acid sequences" *Proceedings of the National Academy of Sciences* 78(6):3824-3828 (1981).
Hoshijima et al. "Chronic suppression of heart-failure progression by a pseudophosphorylated mutant of phospholamban via in vivo cardiac rAAV gene delivery" *Nature Medicine* 8(8):864-871 (2002).
International Preliminary Report on Patentability corresponding to International Patent Application No. PCT/US2016/018746 (7 pages) (dated Aug. 22, 2017).
Karlin et al. "Applications and statistics for multiple high-scoring segments in molecular sequences" *Proceedings of the National Academy of Sciences* 90(12):5873-5877 (1993).
Kawakami et al. "Cloning of the gene coding for a shared human melanoma antigen recognized by autologous T cells infiltrating into tumor" *Proceedings of the National Academy of Sciences* 91(9):3515-3519 (1994).
Kawakami et al. "Identification of the Immunodominant Peptides of the MART-1 Human Melanoma Antigen Recognized by the Majority of HLA-A2-restricted Tumor Infiltrating Lymphocytes" *The Journal of Experimental Medicine* 180(1):347-352 (1994).
Kyte et al. "A Simple Method for Displaying the Hydropathic Character of a Protein" *Journal of Molecular Biology* 157(1):105-132 (1982).
Levine "The Tumor Suppressor Genes" *Annual Review of Biochemistry* 62:623-651 (1993).
Li et al. "Construction of phospholamban antisense RNA recombinant adeno-associated virus vector and its effects in rat cardiomyocytes" *Acta Pharmacologica Sinica* 26(1):51-55 (2005).
Needleman et al. "A General Method Applicable to Search for Similarities in the Amino Acid Sequence of Two Proteins" *Journal of Molecular Biology* 48(3):443-453 (1970).
Pal et al. "Immunization with the *Chlamydia trachomatis* major outer membrane protein, using adjuvants developed for human vaccines, can induce partial protection in a mouse model against a genital challenge" *Vaccine* 24(6):766-775 (2006) (Abstract Only).
Pearson et al. "Improved tools for biological sequence comparison" *Proceedings of the National Academy of Science* 85(8):2444-2448 (1988).
Puttaraju et al. "Spliceosome-mediated RNA trans-splicing as a tool for gene therapy" *Nature Biotechnology* 17(3):246-252 (1999).
Robbins et al. "Recognition of Tyrosinase by Tumor-infiltrating Lymphocytes from a Patient Responding to Immunotherapy" *Cancer Research* 54(12):3124-3126 (1994).
Rosenberg "The Immunotherapy of Solid Cancers Based on Cloning the Genes Encoding Tumor-Rejection Antigens" *Annual Review of Medicine* 47(1):481-491 (1996).
Rosenberg et al. "A New Era for Cancer Immunotherapy Based on the Genes that Encode Cancer Antigens" *Immunity* 10(3):281-287 (1999).
Sharp et al. "RNA interference—2001" *Science* 287(5462):2431-2433 (2000).
Smith et al. "Comparison of Biosequences" *Advances in Applied Mathematics* 2:482-489 (1981).
Tinsley et al. "Amelioration of the dystrophic phenotype of mdx mice using truncated utrophin transgene" *Nature* 384(6607):349-353 (1996).
Tyle "Iontophoretic Devices for Drug Delivery" *Pharmaceutical Research* 3(6):318-326 (1986).
Vincent et al. "Long-term correction of mouse dystrophic degeneration by adenovirus-mediated transfer of a minidystrophin gene" *Nature Genetics* 5:130-134 (1993).
Wang et al. "Adeno-associated virus vector carrying human minidystrophin genes effectively ameliorates muscular dystrophy in mdx mouse model" *Proceedings of the National Academy of Sciences* 97(25):13714-13719 (2000).

* cited by examiner ively. The plaque-purified clones designated as C5 and
METHODS AND COMPOSITIONS FOR ATTENUATED CHLAMYDIA AS VACCINE AND VECTOR

STATEMENT OF PRIORITY

This application is a 35 U.S.C. § 371 national phase application of International Application Serial No. PCT/US2016/018746, filed Feb. 19, 2016, which claims the benefit, under 35 U.S.C. § 119 (e), of U.S. Provisional Application Ser. No. 62/118,961, filed Feb. 20, 2015, the entire contents of which are incorporated by reference herein.

STATEMENT OF GOVERNMENT SUPPORT

The present invention was made with government support under grant numbers R01AI064537 and R01AI 047997 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 9237-54 ST25.txt, 16,655 bytes in size, generated on Aug. 16, 2017 and filed via EFS-Web, is provided in lieu of a paper copy. This Sequence Listing is incorporated by reference into the specification for its disclosures.

FIELD OF THE INVENTION

The present invention relates to treatment/prevention of chlamydial infection and disease and/or to the use of a *Chlamydia* cell as a vector.

BACKGROUND OF THE INVENTION

*Chlamydia trachomatis* is an obligate intracellular Gram-negative bacterium that is the leading cause of bacterial sexually transmitted disease worldwide. The majority of genital chlamydial infections are initially asymptomatic and untreated, despite the availability of effective antimicrobial therapy, and may lead to severe complications such as pelvic inflammatory disease, ectopic pregnancy and infertility. Additionally, the incidence rates of genital chlamydial infections have increased over the last decade, indicating the need for an effective chlamydial vaccine.

The present invention overcomes previous shortcomings in the art by providing methods and compositions employing attenuated *Chlamydia* cells for the treatment and/or prevention of chlamydial infection and disease.

SUMMARY OF THE INVENTION

In one aspect, the present invention provides an isolated *Chlamydia trachomatis* cell comprising a) a substitution at Q117 (e.g., Q117E) in open reading frame CT849, wherein said amino acid numbering is based on the amino acid sequence of SEQ ID NO:1; and b) a G216* mutation (* means a stop codon is incorporated into the nucleotide sequence in place of the codon that is translated into G216 in the wild type sequence) and/or a substitution at G322 (e.g., G322R) in open reading frame CT389, wherein said amino acid numbering is based on the amino acid sequence of SEQ ID NO:2, wherein said *Chlamydia trachomatis* cell has a phenotype due to said substitution of (a) and said mutation and/or substitution of (b) of attenuated pathogenicity. In some embodiments, the isolated *Chlamydia trachomatis* cell can further comprise a mutation in the open reading frame CT135 selected from the group consisting of: a) a CT135fs29 mutation; b) a CT135E88* mutation (* means a stop codon is incorporated into the nucleotide sequence in place of the codon that is translated into E88 in the wild type sequence); c) a CT125fs145 mutation; and d) any combination of (a)-(c) above, wherein said amino acid numbering is based on the amino acid sequence of SEQ ID NO:3.

In further aspects of this invention, the *Chlamydia trachomatis* cell of this invention can further comprise a heterologous nucleic acid molecule.

Also provided herein is a method of treating and/or preventing a disease or disorder associated with or caused by chlamydial infection in a subject, comprising administering to the subject an effective amount of the *Chlamydia trachomatis* cell of this invention Further aspects of this invention include a method of eliciting an immune response to *Chlamydia* in a subject, comprising administering to the subject an effective amount of the isolated *Chlamydia trachomatis* cell of this invention The present invention also provides a method of reducing the likelihood of infertility due to *Chlamydia* infection in a subject, comprising administering to the subject an effective amount of the isolated *Chlamydia trachomatis* cell of this invention.

Further provided herein is a method of reducing the incidence of hydrosalpinx due to *Chlamydia* infection in a subject, comprising administering to the subject an effective amount of the isolated *Chlamydia trachomatis* cell of this invention.

Another aspect of this invention includes a method of delivering a heterologous nucleic acid molecule to a subject, comprising administering to the subject the *Chlamydia trachomatis* cell of this invention, wherein the *Chlamydia trachomatis* cell comprises a heterologous nucleic acid molecule. In some embodiments, the heterologous nucleic acid molecule can encode a therapeutic protein and/or therapeutic RNA.

Additional aspects of this invention include a method of inducing an immune response to an immunogen in a subject, comprising administering to the subject the *Chlamydia trachomatis* cell of this invention wherein the *Chlamydia trachomatis* cell comprises a heterologous nucleic acid molecule and the heterologous nucleic acid molecule encodes the immunogen. In particular embodiments, the immunogen can be a human immunodeficiency virus (HIV) protein or immunogenic fragment thereof.

FIG. 3. Microscopic observation of oviduct dilation induced by the CMG0 and CMG28 populations and plaque-purified clones. The oviduct tissues of mice infected with the four pairs of CMG0 and CMG28 organisms were harvested and subjected to H&E staining for microscopic evaluation of oviduct dilation. (A) Representative images from each group taken under a 4× objective lens, with panels a and b from mice infected with CMG0 and CMG28 populations, respectively, and panels c-h from the three pairs of plaque-purified clone-infected mice, respectively, as indicated on top of each image. Uterine horn (UH), normal oviduct, and ovary tissues were marked as shown in the figure. Dilated oviducts are indicated with white lines with arrowheads at both ends. The horizontal bar at the right bottom of each image represents a physical distance of 0.5 mm. (B) Severity of lumenal dilation was scored as described herein and listed along the Y-axis. The four pairs of *C. muridarum* organisms were listed along the X-axis. Note that all CMG28 organisms induced more significant oviduct lumenal dilation than their CMG0 counterparts with the exception of the CMG0.1.1 and CMG28.38.1 pair. *p<0.05 and **p<0.01 (Wilcoxon rank-sum test). Score (Rank sum test): G0 vs G28: P=0.00507164; G0.1.1 vs G28.38.1: P=0.309524; G0.21.3 vs G28.12.3: P=0.01587302; G0.10.1 vs G28.54.1: P=0.0079365.

FIG. 4. Live chlamydial organism shedding from mouse lower genital tract following infection with the CMG0 and CMG28 populations and plaque-purified clones. C3H/Hej mice were intravaginally infected with four pairs of *C. muridarum* CMG0 (solid square) and CMG28 (open square) organisms described in FIG. 2 and as indicated above the corresponding plots. On different days after infection as shown along the X-axis, vaginal swabs were taken for titrating live organisms on HeLa cell monolayers. The live organisms recovered from each swab are expressed as $Log_{10}$ IFUs along the Y-axis (panels a, c, e & g). The percent of mice remaining positive for shedding live organisms at each time point was plotted along the Y-axis in panels b, d, f & h. Note that there are no significant differences in live organism sheddings from the lower genital tracts between mice infected with the CMG0 and CMG28 organisms.

FIG. 5. Live chlamydial organism recovery from mouse genital tract tissues following infection with the CMG0 and CMG28 populations. C3H/HeJ mice intravaginally infected with CMG0 (solid bar, n=5) or CMG28 (open bar, n=5) population organisms were sacrificed on day 14 after infection. Vaginal swab were taken prior to mouse sacrifice. The entire genital tract tissue was harvested from each mouse and divided into the lower genital tract (LGT) vagina/cervix (VC) and the upper genital tract (UGT) uterus/uterine horn (UH) and oviduct/ovary (OV) sections as listed along the X-axis. Each tissue section was homogenized for titrating live *C. muridarum* organisms. Vaginal swabs were similarly titrated for live organisms. $Log_{10}$ IFUs were used to calculate mean and SD for each group as displayed along the Y-axis. Note that the number of live organisms recovered from mice infected with either CMG0 or CMG28 was similar without any significant difference (Kruskal-Wallis test).

FIG. 6. Oviduct inflammatory infiltration induced by the CMG0 and CMG28 populations and plaque-purified clones. The oviduct tissues from mice infected with the CMG0 and CMG28 populations and plaque-purified clones described in FIG. 2 were subjected to H&E staining as described in FIG. 3 for evaluating inflammatory histopathology. (A) Representative images from each group taken under 10× (left panels) and 100× (right panels) objective lens. White rectangles in the 10× objective lens images indicated the same areas from which the right images were taken under 100× objective lens. (B) The severity of inflammatory infiltration in oviduct tissue was scored as described herein and listed along the Y-axis. The four pairs of *C. muridarum* organisms were listed along the X-axis. Note that all CMG28 organisms induced more significant oviduct inflammatory infiltration than their CMG0 counterparts with the exception of the CMG0.1.1 and CMG28.38.1 pair. *p<0.05 and **p<0.01 (Wilcoxon rank-sum test). Score (Rank sum test): G0 vs G28: P=0.01016864; G0.1.1 vs G28.38.1: P=0.0555556; G0.21.3 vs G28.12.3: P=0.01587302; G0.10.1 vs G28.54.1: P=0.01587302.

FIG. 7. Attenuated chlamydial organism induces protection against wild type chlamydial infection and pathology. Immunization of C3H/HeJ mice with attenuated G28.52.1 induced protection against wild type *C. muridarum* (G0.1.1) infection and pathology.

FIG. 8. *Chlamydia muridarum* last long periods of time in the gastrointestinal (GI) tract. Mice were infected with luciferase-expressing *C. muridarum* intragastrically (top 2 rows), intrarectally (middle), or intravenously (bottom). Chemiluminescent signals were monitored on various days after infection as indicated on top of the figure. For each infection group, images from a representative mouse are shown with the whole body image first and the white square-highlighted area shown below the image.

DETAILED DESCRIPTION OF THE INVENTION

Figure 1:
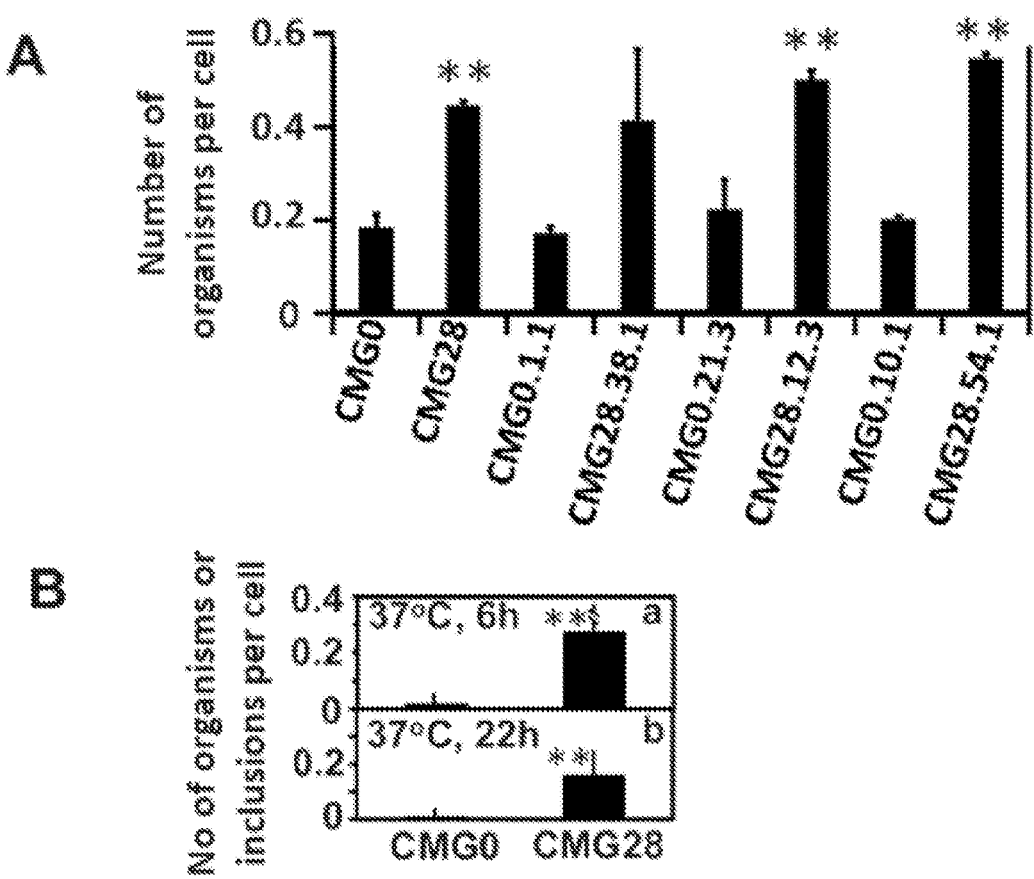
FIG. 1. Attachment of CMG0 and CMG28 populations and plaque-purified clones to cultured HeLa cells. (A) The same number of CMG0 and CMG28 organisms, as listed along X-axis, were inoculated to HeLa cell monolayers under the unassisted infection conditions. The infected cells were washed and processed for immunofluorescence detection of the remaining chlamydial organisms at 1 h after incubation at 4° C. (A) or 6 h (B, panel a) or 22 h (B, panel b) after incubation at 37° C. The cell-associated chlamydial organisms or inclusions were counted and expressed as the number of chlamydial organisms or inclusions per cell, as shown along the Y-axis. The 37° C. incubation condition was only applied to the CMG0 and CMG28 population cultures (B). Note that the numbers of chlamydial organisms or inclusions per cell in the cultures infected with the CMG28 organisms were significantly higher than those with the CMG0 organisms. All experiments were repeated three times. **p<0.01 (Kruskal-Wallis test). T test: G0 vs G28, p=0.000191463; G0.1.1 vs G28.38.1, p=0.061030481; G0.21.3 vs G28.12.3, p=005418979; G0.10.1 vs G28.54.1, p=0.00004688.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "consists essentially of" (and grammatical variants) means that an immunogenic composition of this invention comprises no other material immunogenic agent other than the indicated agents. The term "consists essentially of" does not exclude the presence of other components in the composition such as adjuvants, immunomodulators, and the like.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references cited herein are incorporated by reference herein.

The present invention is based on the discovery of a Chlamydia organism comprising mutations that impart a phenotype of attenuated pathogenicity, which has utility as a whole cell vaccine as well as a vector for delivering nucleic acid molecules to a subject. Thus, in one embodiment, the present invention provides an isolated Chlamydia trachomatis cell comprising: a) a substitution at Q117 in open reading frame CT849, wherein said amino acid numbering is based on the amino acid sequence of CT849 as provided herein as SEQ ID NO:1; and b) a G216* mutation and/or a substitution at G322 in open reading frame CT389, wherein said amino acid numbering is based on the amino acid sequence of CT389 as provided herein as SEQ ID NO:2, wherein said Chlamydia trachomatis cell has a phenotype due to said substitution of (a) and said mutation and/or substitution of (b) of attenuated pathogenicity.

In some embodiments of this invention, the substitution in open reading frame CT849 can be Q117E. In some embodiments, the substitution at Q117 can be with any other amino acid, such that the phenotype of attenuated pathogenicity is retained. The substitutions can be conservative substitutions or non-conservative substitutions. Examples of amino acids that can be substituted are listed in Table 4 and Table 5.

In some embodiments of this invention, the substitution in open reading frame CT389 can be G322R. In some embodiments, the substitution at G322 can be with any other amino acid, such that the phenotype of attenuated pathogenicity is retained. The substitutions can be conservative substitutions or non-conservative substitutions. Examples of amino acids that can be substituted are listed in Table 4 and Table 5.

As used herein, "attenuated pathogenicity" means that infection with the Chlamydia cell of this invention results in reduced levels of hydrosalpinx and/or reduced levels of inflammatory cytokines (i.e., reduced inflammatory stimulation), relative to a Chlamydia cell lacking the substitutions and/or mutations described herein.

In further embodiments, the he isolated Chlamydia trachomatis cell of this invention can further comprise a mutation in the open reading frame CT135 selected from the group consisting of: a) a CT135fs29 mutation; b) a CT135E88* mutation; c) a CT125fs145 mutation; and d) any combination of (a)-(c) above, wherein said amino acid numbering is based on the amino acid sequence of CT135 provided herein as SEQ ID NO:3.

In some embodiments, the isolated Chlamydia trachomatis cell of this invention can further comprise a heterologous nucleic acid molecule. Such a heterologous nucleic acid molecule can encode a therapeutic protein or peptide and/or a functional RNA molecule.

The present invention further provides a composition comprising the isolated Chlamydia trachomatis cell of this invention and a pharmaceutically acceptable carrier.

In further embodiments, the present invention provides a method of treating and/or preventing a disorder associated with or caused by chlamydial infection and/or to ameliorate the pathological conditions associated with chlamydial infection in a subject, comprising administering to the subject an effective amount of the isolated Chlamydia trachomatis cell of this invention.

Also provided herein is a method of eliciting an immune response to Chlamydia in a subject, comprising administering to the subject an effective amount of the isolated Chlamydia trachomatis cell of this invention.

Furthermore, the present invention provides a method of reducing the likelihood of infertility due to Chlamydia infection in a subject, comprising administering to the subject an effective amount of the isolated Chlamydia trachomatis cell of this invention.

In another embodiment, the present invention provides a method of reducing the incidence of hydrosalpinx due to Chlamydia infection in a subject, comprising administering to the subject an effective amount of the isolated Chlamydia trachomatis cell this invention In some embodiments, the above methods can further comprise administering an adjuvant and/or an immunostimulatory agent to the subject.

Further provided herein is a method of delivering a heterologous nucleic acid molecule to a subject, comprising administering to the subject the Chlamydia trachomatis cell of this invention, wherein the cell comprises a heterologous nucleic acid molecule. In some embodiments, the heterologous nucleic acid molecule can encode a therapeutic protein, peptide and/or RNA molecule.

In some embodiments, the Chlamydia trachomatis cell of this invention can be administered to mucosal tissue of the subject.

Additionally provided herein is a method of inducing an immune response to an immunogen in a subject, comprising administering to the subject the Chlamydia trachomatis cell of this invention, wherein the cell comprises a heterologous nucleic acid molecule that encodes the immunogen. In some embodiments, the immunogen can be a human immunodeficiency virus (HIV) protein or immunogenic fragment thereof.

In some embodiments, a *Chlamydia trachomatis* cell of this invention, comprising a) a substitution at Q117 in open reading frame CT849, wherein said amino acid numbering is based on the amino acid sequence of CT849 as provided herein as SEQ ID NO:1; and b) a G216* mutation and/or a substitution at G322 in open reading frame CT389, wherein said amino acid numbering is based on the amino acid sequence of CT389 as provided herein as SEQ ID NO:2 and also comprising a heterologous nucleic acid molecule, can be administered to the gastrointestinal (GI) tract of a subject (e.g., a subject in need). In some embodiments, the heterologous nucleic acid molecule can encode a therapeutic protein or RNA that can be produced in the GI tract, for example, to treat, ameliorate and/or prevent a disease or disorder of the GI tract of the subject.

In some embodiments, a *Chlamydia trachomatis* cell of this invention, comprising a) a substitution at Q117 in open reading frame CT849, wherein said amino acid numbering is based on the amino acid sequence of CT849 as provided herein as SEQ ID NO:1; and b) a G216* mutation and/or a substitution at G322 in open reading frame CT389, wherein said amino acid numbering is based on the amino acid sequence of CT389 as provided herein as SEQ ID NO:2 and that does not comprise a heterologous nucleic acid molecule can be administered to the GI tract of a subject to induce an immune response in the GI tract of the subject (e.g., a subject in need thereof).

In some embodiments, a *Chlamydia trachomatis* cell that does not comprise a) a substitution at Q117 in open reading frame CT849, wherein said amino acid numbering is based on the amino acid sequence of CT849 as provided herein as SEQ ID NO:1; and b) a G216* mutation and/or a substitution at G322 in open reading frame CT389, wherein said amino acid numbering is based on the amino acid sequence of CT389 as provided herein as SEQ ID NO:2 and that comprises a heterologous nucleic acid molecule, can be administered to the gastrointestinal (GI) tract of a subject (e.g., a subject in need). In some embodiments, the heterologous nucleic acid molecule can encode a therapeutic protein or RNA that can be produced in the GI tract, for example, to treat, ameliorate and/or prevent a disease or disorder of the GI tract of the subject.

In some embodiments, a *Chlamydia trachomatis* cell that does not comprise a) a substitution at Q117 in open reading frame CT849, wherein said amino acid numbering is based on the amino acid sequence of CT849 as provided herein as SEQ ID NO:1; and b) a G216* mutation and/or a substitution at G322 in open reading frame CT389, wherein said amino acid numbering is based on the amino acid sequence of CT389 as provided herein as SEQ ID NO:2 and that does not comprise a heterologous nucleic acid molecule can be administered to the GI tract of a subject to induce an immune response in the GI tract of the subject (e.g., a subject in need thereof).

Additionally provided herein is a method of inducing an immune response to an immunogen in a subject, comprising administering to the subject the *Chlamydia trachomatis* cell of this invention, wherein the cell comprises a heterologous nucleic acid molecule that encodes the immunogen. In some embodiments, the immunogen can be a human immunodeficiency virus (HIV) protein or immunogenic fragment thereof.

Further provided herein is a method of treating a gastrointestinal disorder in a subject, comprising administering to the gastrointestinal tract of the subject the *Chlamydia trachomatis* cell and/or composition of this invention. In one nonlimiting example, a *Chlamydia trachomatis* cell of this invention comprising a nucleotide sequence encoding human interleukin 22 (IL-22) can be administered to a subject of this invention (e.g., a subject in need thereof) to treat, ameliorate and/or prevent colitis in the subject.

The present invention also provides an isolated CT389 polypeptide of this invention comprising a G216* nonsense mutation and/or a substitution at G322 in open reading frame CT389, wherein said amino acid numbering is based on the amino acid sequence of CT389 as provided herein as SEQ ID NO:2, as a vaccine to stimulate an immune response in a subject (e.g., a subject in need thereof). Thus, a method is also provided herein of inducing an immune response in a subject (e.g., a subject in need thereof), comprising administering to the subject the isolated CT389 polypeptide of this invention.

The present invention additionally provides a method of treating, ameliorating and/or preventing a disease or disorder due to *Chlamydia* infection, comprising administering to the subject the isolated CT389 polypeptide of this invention.

By "reducing the likelihood of infertility due to *Chlamydia* infection" is meant that a subject of this invention to whom the immunogenic compositions of this invention are administered is prevented from becoming infertile as a result of *Chlamydia* infection or that the likelihood that the subject will become infertile as a result of being infected by *Chlamydia* is reduced as compared to the likelihood that an untreated subject will become infertile as a result of being infected by *Chlamydia*. That infertility is prevented or its likelihood as a result of *Chlamydia* infection is reduced in a subject can be determined according to protocols described herein and as would be well known in the art.

Hydrosalpinx is a result of tubal blockade and subsequent retention of fluid exudate within the tubal lumen. Given that the patency of oviducts is important to allow fertilization of the ovum and sperm, and that the hydrosalpinx fluid is toxic to the ovum, the presence of hydrosalpinx serves as an indirect marker of infertility.

By "reducing the incidence of hydrosalpinx due to *Chlamydia* infection" is meant that a subject of this invention to whom the immunogenic compositions of this invention are administered will be prevented from or protected against developing hydrosalpinx due to *Chlamydia* infection or has a reduced likelihood of developing hydrosalpinx due to *Chlamydia* infection or has a lesser degree of hydrosalpinx due to *Chlamydia* infection as compared to an untreated subject infected by *Chlamydia*. That hydrosalpinx due to *Chlamydia* infection is prevented or its incidence and/or degree are reduced in a subject can be determined according to protocols described herein and as would be well known in the art.

A *Chlamydia* cell of this invention can be *Chlamydia trachomatis, Chlamydia muridarum, Chlamydia pneumoniae Chlamydia psittaci, Chlamydophila abortus* and/or *Chlamydia caviae*. A cell of this invention can be from any species of *Chlamydia, Chlamydophila* and/or *Parachlamydia*.

The cells of this invention can be modified according to art-known methods and/or administered in an adjuvant in order to increase immunogenicity. Methods of increasing the antigenicity or immunogenicity of a protein or peptide (e.g., on the cell surface and/or produced by the cell) are well known in the art. The immunogenicity of the cell can also be increased through the inclusion of one or more adjuvants in addition to the cell of this invention. The adjuvant can be administered with the cell, before administration of the cell, after administration of the cell, or any combination thereof.

Thus, the compositions employed in the methods of this invention can comprise, consist essentially of and/or consist of a *Chlamydia trachomatis* cell of this invention either alone or in combination with a chlamydial protein and/or immunogenic fragment and or epitope thereof, as well as nucleic acids encoding the chlamydial protein and/or immunogenic fragment and/or epitope thereof and can further comprise, consist essentially of and/or consist of an adjuvant.

In some embodiments, such compositions can further comprise one or more than one adjuvant in the form of an amino acid sequence, and/or in the form or a nucleic acid encoding an adjuvant. The adjuvant, in the form of an amino acid sequence, can be a component of a chlamydial cell of this invention and/or a separate component of the composition comprising one or more chlamydial polypeptides and/or fragments and/or epitopes thereof. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of this invention. An adjuvant of this invention can be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with the cells and/or compositions of this invention to enhance, improve or otherwise modulate an immune response in a subject without deleterious effect on the subject.

In further embodiments, an adjuvant of this invention can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, and/or may be an insoluble suspension of acylated tyrosine, or acylated sugars, cationically or anionically derivatized polysaccharides, or polyphosphazenes.

Other adjuvants are well known in the art and include MF 59, LT-K63, LT-R72 (Pal et al., Vaccine 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycotate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153 (the entire contents of which are incorporated herein by reference), or a less reactogenic composition where the QS21 is quenched with cholesterol as disclosed in PCT publication number WO 96/33739 (the entire contents of which are incorporated herein by reference). A particularly potent adjuvant formulation involving QS21 3D-MPL & tocopherol in an oil in water emulsion is described in PCT publication number WO 95/17210 (the entire contents of which are incorporated herein by reference). In addition, a nucleic acid molecule of this invention can include an adjuvant by comprising a nucleotide sequence encoding an antigen of this invention and a nucleotide sequence that provides an adjuvant function, such as CpG sequences, Such CpG sequences, or motifs, are well known in the art.

An adjuvant of this invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of an immunogenic chlamydial composition and/or cell of this invention to a subject.

Furthermore, any combination of adjuvants, such as immunostimulatory cytokines, can be co-administered to the subject before, after and/or concurrent with the administration of an immunogenic chlamydial composition and/or cell of this invention. For example, combinations of immunostimulatory cytokines, can consist of two or more immunostimulatory cytokines of this invention, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

Pharmaceutical compositions comprising the *Chlamydia* cells, immunogenic chlamydial proteins, fragments and or epitopes of this invention and a pharmaceutically acceptable carrier are also provided. The compositions described herein can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response), Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

As set forth herein, the term "immunogenic fragment" means a fragment (e.g., a peptide) of a protein that can stimulate either humoral or cellular immune responses in the subject. An immunogenic fragment of this invention can comprise, consist essentially of and/or consist of one, two, three, four or more epitopes of a protein of this invention. An immunogenic fragment can be any fragment of contiguous amino acids of a protein of this invention and can be for example, 5, 10, 15, 20, 25, 30, 35, 40, 45, 50, 75, 100, 150, 200, 250, 300, 350, 400, 450, 500 or 550 amino acids in length. Identification of any such immunogenic fragments is routine in the art.

As noted herein, an immune response elicited or produced by carrying out the methods of this invention can be a protective immune response, a cellular immune response, a humoral immune response, a Th1 immune response, a Th2 immune response and any combination thereof.

To stimulate the humoral arm of the immune system, i.e., the production of antigen-specific antibodies, an immunogenic fragment can include at least about 5-10 contiguous amino acid residues of the full-length molecule, or at least about 15-25 contiguous amino acid residues of the full-length molecule, or at least about 20-50 or more contiguous amino acid residues of the full-length molecule, that define one or more epitopes, or any integer between five amino acids and the full-length sequence, provided that the fragment in question retains immunogenic activity, as measured by any art-known assay, such as, e.g., the ones described herein and/or those known in the art.

Regions of a given polypeptide that include an epitope can be identified using any number of epitope mapping techniques, well known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci.* USA 81:3998-4002; Geysen et al. (1986) *Molec. Immunol.* 23:709-715, all incorporated herein by reference in their entireties.

Similarly, conformational epitopes are readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids, and these are not typically predicted by the above-described methods for identifying humoral epitopes. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenic fragments can also be identified based on their ability to stimulate lymphocyte proliferation in response to stimulation by various fragments from the antigen of interest.

The term "epitope" as used herein refers to at least about 3 to about 5, or about 5 to about 10 or about 5 to about 15, and not more than about 100, 500 or 1,000 amino acids (or any integer therebetween), which define a sequence that by itself or as part of a larger sequence, binds to an antibody generated in response to such sequence and/or stimulates a cellular immune response. There is no critical upper limit to the length of the fragment, which can comprise nearly the full-length of the protein sequence, or even a fusion protein comprising two or more epitopes from a single or multiple chlamydial proteins. An epitope for use in the present invention is not limited to a polypeptide having the exact sequence of the portion of the parent protein from which it is derived. Indeed, there are many known strains or isolates of *Chlamydia* and there are several variable domains that exhibit relatively high degrees of variability between isolates. Thus, the term "epitope" encompasses sequences identical to the native sequence, as well as modifications to the native sequence, such as deletions, additions and substitutions (generally, but not always, conservative in nature) that are readily produced and/or identified as epitopes according to methods standard in the art.

As used herein, the term "polypeptide" or "protein" is used to describe a chain of amino acids that correspond to those encoded by a nucleic acid. A polypeptide or protein of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences of this invention are presented in the amino to carboxy direction, from left to right. Nucleotide sequences are presented herein, in the 5' to 3' direction, from left to right. The nucleic acids of this invention can be either single or double stranded (i.e., including the complementary nucleic acid). A nucleic acid of this invention can be the complement (e.g., complementary to the full length or only to a portion) of a nucleic acid described herein.

A "biologically active fragment" includes a polypeptide of this invention that comprises a sufficient number of amino acids to have one or more of the biological activities of the polypeptides of this invention. Such biological activities can include, but are not limited to, in any combination, binding activity and/or immunogenic activity, as well as any other activity now known or later identified for the polypeptides and/or fragments of this invention.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention (e.g., immunogenicity) according to the methods described herein, which are routine methods for testing activities of polypeptides, and/or according to any art-known and routine methods for identifying such activities. Such production and testing to identify biologically active fragments and/or immunogenic fragments of the polypeptides described herein would be well within the scope of one of ordinary skill in the art and would be routine.

The term "isolated" as used herein means the protein or polypeptide or immunogenic fragment or nucleic acid or cell of this invention is sufficiently free of contaminants or cell components or other biological components with which polypeptides and/or nucleic acids and/or cells normally occur. "Isolated" does not mean that the preparation is technically pure (homogeneous), but it is sufficiently pure to provide the polypeptide or nucleic acid in a form in which it can be used therapeutically. Furthermore, an isolated cell is a cell that has been separated from other components with which it is normally associated in nature. For example, an isolated cell can be a cell in culture medium and/or a cell in a pharmaceutically acceptable carrier of this invention.

The methods of this invention can be practiced to treat and/or prevent infection and/or disease caused by any chlamydial species that can infect a subject of this invention, including, for example *Chlamydia trachomatis*, *Chlamydia pneumoniae*, *Chlamydia muridarum*, *Chlamydia psittaci*, *Chlamydophila abortus* and/or *Chlamydia caviae*.

The terms "prevent," "preventing," and "prevention" and like terms are used herein to include imparting any level of prevention or protection which is of some benefit to a subject, such that there is a reduction in the incidence and/or the severity of the disease in a treated subject, regardless of whether the protection or reduction in incidence and/or severity is partial or complete.

By "prime," "primed" or "priming" (and grammatical variations thereof) as used herein, it is meant to initiate an active immune response that is less than protective until a second dose (booster) is given at a later time.

"Boost" or "booster" means a second immunization, after an initial (or "priming") immunization that enhances the immune response of the subject. Therefore, in some embodiments, the invention provides a composition that produces an anamnestic response against a *Chlamydia* infection, in a sensitized subject, comprising an anamnestic response-inducing amount of a *Chlamydia* protein immunizing component. As used herein, the term "anamnestic response" means a secondary (booster) immune response in a sensitized subject. By "sensitized subject" is meant a subject that has previously been in contact with a chlamydial antigen or antigens, either by natural exposure or by vaccination (primary immunization) with *Chlamydia* protein immunizing components.

The terms "reduce," "reduced," "reducing," and "reduction" (and grammatical variations thereof), as used herein, describe a decrease in a chlamydial infection- or disease-related parameter or symptom that is of some therapeutic value or benefit to the subject.

As used herein, the terms "elicit" or "induce" or "produce" (or grammatical variations thereof) in the context of an immune response against *Chlamydia* are intended to encompass the activation and/or stimulation of cells and other components of the immune system in a subject to ameliorate the effects of chlamydial infection in the subject. The immune response of this invention can be a protective immune response, for example, as desired in vaccination methods to treat and/or prevent infection. Protection is not required if there is some other purpose for inducing the immune response, for example, for research purposes or to produce antibody for passive immunizations or as a reagent (e.g., to detect, isolate and/or identify *Chlamydia* species).

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the term "ameliorate" refers to the ability to make better, or more tolerable, a condition such as a chlamydial infection or a disorder associated with a chlamydial infection.

As used herein "effective response" or "responding effectively" means a positive or beneficial response to a particular treatment in contrast to a "lack of an effective response" which can be an ineffectual, negative or detrimental response as well as the lack of a positive or beneficial response. An effective response or lack of effective response (i.e., ineffective response) is detected by evaluation, according to known protocols, of various immune functions (e.g., cell-mediated immunity, humoral immune response, etc.) and pharmacological and biological functions as would be known in the art.

"Effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

The terms "immunogenic amount" or "effective immunizing dose," as used herein, unless otherwise indicated, mean a dose of a composition of this invention sufficient to induce an immune response (which can be a protective response) in the treated subject that is greater than the inherent immunity of non-immunized subjects. An immunogenic amount or effective amount or effective immunizing dose in any particular context can be routinely determined using methods known in the art.

In some embodiments, an effective immunizing dose or immunogenic amount or effective amount can comprise one or more (e.g., two or three or four or more) doses of the immunogenic composition of this invention at any time interval (e.g., hourly, daily, weekly, monthly, yearly, etc.) so as to achieve and/or maintain the desired level of protection and/or other therapeutic benefit.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

The terms "protective immunity" or "protective immune response," as used herein, are intended to mean that the subject mounts an active immune response to the immunogenic composition and/or that the subject has been provided with passive immunity, such that upon subsequent exposure or a challenge, the animal is able to resist and/or overcome infection and/or disease. Thus, a protective immune response will decrease the incidence of morbidity and/or mortality from subsequent exposure to the chlamydial pathogens of this invention.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985).

Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

In some embodiments, "cross-species immunity," e.g., immunity with respect to multiple species of *Chlamydia* (e.g., *Chlamydia muridarum, Chlamydia trachomatis*, etc.) (e.g., cross-species protective immunity) can be accomplished with the methods of this invention as described herein. Thus, the present invention provides a method of eliciting a cross-species immune response in a subject (e.g., to treat and/or prevent chlamydial infection and/or disease) by administering to the subject an effective amount of the immunogenic chlamydial compositions and/or cells of this invention, thereby eliciting a cross-species immune response to *Chlamydia* species in the subject.

In certain embodiments, employing the methods of this invention provides a reduction in the incidence of hydrosalpinx, oviduct dilatation, and/or cellular infiltration associated with chlamydial infection. Thus, the present invention further provides methods of treating and/or preventing hydrosalpinx, oviduct dilatation, and/or cellular infiltration associated with chlamydial infection in a subject, comprising administering to the subject an immunogenic composition and/or cell of this invention, with our without an adjuvant.

In yet further embodiments, the immune response of this invention can include a Th1 immune response. "Th1" refers to a helper T cell response which involves the production of interferon-gamma (IFN-γ), leading to cell-mediated immunity. In other embodiments, the immune response can include a Th2 immune response. "Th2" refers to a helper T cell response which involves the release of interleukin 4 (IL-4), leading to humoral immunity. See, e.g., U.S. Patent Application Publication No. 2006/0034871 to Grandi et al., incorporated by reference herein in its entirety for its teachings of Th1 and Th2 responses.

In some embodiments, the immune response of this invention includes a gamma interferon (IFN-γ)-dependent protective immune response. Thus the present invention additionally provides a method of eliciting a gamma interferon-dependent protective immune response against *Chlamydia* in a subject, comprising administering to the subject an effective amount of an immunogenic composition and/or cell of this invention, with or without an adjuvant.

A "subject" of this invention includes any animal susceptible to infection by a *Chlamydia* species. Such a subject can be a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species and in particular embodiments, is a human. A "subject in need thereof" is a subject known to be, or suspected of being, infected with, or at risk of being infected with, *Chlamydia*. A subject of this invention can also include a subject not previously known or suspected to be infected by *Chlamydia* or in need of treatment for *Chlamydia* infection. For example, a subject of this invention can be administered the compositions of this invention even if it is not known or suspected that the subject is infected with *Chlamydia* (e.g., prophylactically). A subject of this invention is also a subject known or believed to be at risk of infection by *Chlamydia*.

In certain embodiments, the fragments and/or polypeptides of this invention can be fused with a "carrier" protein or peptide to produce a fusion protein. For example, the carrier protein or peptide can be fused to a polypeptide and/or fragment of this invention to increase the stability thereof (e.g., decrease the turnover rate) in the cell and/or subject. Exemplary carrier proteins include, but are not limited to, glutathione-S-transferase or maltose-binding protein. The carrier protein or peptide can alternatively be a reporter protein. For example, the fusion protein can comprise a polypeptide and/or fragment of this invention and a reporter protein or peptide (e.g., green fluorescent protein (GFP), β-glucoronidase, β-galactosidase, luciferase, and the like) for easy detection. As a further alternative, the fusion protein attached to the polypeptides and/or fragments and a carrier protein or peptide can be targeted to a subcellular compartment of interest, i.e., to affect the co-localization of the polypeptide and/or fragment. Any suitable carrier protein as is well known in the art can be used to produce a fusion protein of this invention.

The present invention further includes isolated polypeptides, peptides, proteins and/or fragments that are substantially equivalent to those described for this invention. As used herein, "substantially equivalent" can refer both to nucleic acid and amino acid sequences, for example a mutant sequence, that varies from a reference sequence by one or more substitutions (e.g., substitution with conservative amino acids as are well known in the art), deletions and/or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), or by inspection.

Another suitable algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

The invention further provides homologues, as well as methods of obtaining homologues, of the polypeptides and/or fragments of this invention from other strains of *Chlamydia* and/or other organisms included in this invention. As used herein, an amino acid sequence or protein is defined as a homologue of a polypeptide or fragment of the present invention if it shares significant homology to one of the polypeptides and/or fragments of the present invention. Significant homology means at least 75%, 80%, 85%, 90%, 95%, 98% and/or 100% homology with another amino acid sequence. Specifically, by using the nucleic acids that encode the chlamydial proteins and fragments of this invention (as are known in the art and incorporated by reference herein), as a probe or primer, and techniques such as PCR amplification and colony/plaque hybridization, one skilled in the art can identify homologues of the polypeptides and/or fragments of this invention in *Chlamydia* and/or other organisms on the basis of information available in the art. As one non-limiting example, a listing of *Chlamydia pneumoniae* proteins and the *Chlamydia trachomatis* homologues of these proteins can be found in U.S. Pat. No. 6,822,071, the entire contents of which are incorporated by reference herein for these teachings.

It is further contemplated that the present invention provides a kit comprising the compositions of this invention. It would be well understood by one of ordinary skill in the art that the kit of this invention can comprise one or more containers and/or receptacles to hold the reagents (e.g., cells, antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

It is contemplated that the above-described compositions of this invention can be administered to a subject or to a cell of a subject to impart a therapeutic benefit, such as eliciting an immune response. Thus, as noted above, the present invention further provides a method of eliciting or producing an immune response in a subject, comprising administering to the subject and/or to a cell of the subject an effective amount of an immunogenic composition and/or cell of this invention, with or without an adjuvant of this invention. A cell of the subject can be in vivo or ex vivo and can be, but is not limited to a CD8+ T lymphocyte (e.g., a cytotoxic T lymphocyte), an MHC I-expressing antigen presenting cell, such as a dendritic cell, a macrophage and/or a monocyte. The cell can also be an antigen presenting cell or other class I MHC-expressing cell which can be contacted with the nucleic acids and/or vectors of this invention under conditions whereby the nucleic acid or vector is introduced into the cell by standard methods for uptake of nucleic acid and vectors. The nucleic acid encoding the polypeptide and/or fragment of this invention is then expressed and the polypeptide and/or fragment product is processed within the antigen presenting cell or other MHC I-expressing cell and presented on the cell surface as an MHC I/antigen complex. The antigen presenting cell or other class I MHC-expressing cell is then contacted with an immune cell of the subject which binds the class I MHC/antigen complex and elicits an immune response which treats or prevents *Chlamydia* infection in the subject.

Detection of an immune response in the subject and/or in the cells of the subject can be carried out according to methods standard in the art for detecting a humoral and/or cellular immune response.

As noted above, the compositions of this invention can be administered to a cell of a subject or to a subject either in vivo or ex vivo. For administration to a cell of the subject in vivo, as well as for administration to the subject, the *Chlamydia* cells and/or compositions of this invention can be administered orally, intranasally, intravaginally, intrarectally, intragastrically, intraurethrally, intraocularly, parenterally (e.g., intravenously), by intramuscular injection, by intraperitoneal injection, subcutaneous injection, transdermally, extracorporeally, topically or the like. Also, in some embodiments, the compositions of this invention can be pulsed onto dendritic cells, which are isolated or grown from a subject's cells, according to methods well known in the art, or onto bulk peripheral blood mononuclear cells (PBMC) or various cell subfractions thereof from a subject.

The exact amount(s) of the composition(s) of this invention that will be required will vary from subject to subject, depending on the species, age, weight and general condition of the subject, the particular composition used, its mode of administration and the like. Thus, it is not possible to specify an exact amount for every composition of this invention. However, effective amount can be determined by one of ordinary skill in the art using only routine experimentation given the teachings herein and that are well known in the art.

As an example, to a subject diagnosed with *Chlamydia* infection or known to be at risk of being infected with *Chlamydia* or in whom it is desirable to induce an immune response to *Chlamydia*, about 1000 to about 1,000,000 of the *Chlamydia* cells of this invention can be administered (e.g., intravaginally and/or intranasally for inducing mucosal immunity) and can be in combination with an adjuvant, at one to three hour/day/week intervals until an evaluation of the subject's clinical parameters indicate that the subject is not infected by *Chlamydia* and/or the subject demonstrates the desired immunological response.

Alternatively, a polypeptide and/or fragment of this invention can be pulsed onto dendritic cells at a concentration of between about 10-100 μM and the dendritic cells can be administered to the subject intravenously at the same time intervals. The treatment can be continued or resumed if the subject's clinical parameters indicate that *Chlamydia* infection is present and/or the desired immunological response is diminished or no longer present and can be maintained until the infection is no longer detected by these parameters and/or until the desired immunological response is achieved or re-established.

Parenteral administration of the peptides, polypeptides, nucleic acids and/or vectors of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, intranasal, subcutaneous, intramuscular, intraperitoneal, intravenous and intratracheal routes, as well as a slow release or sustained release system such that a constant dosage is maintained. See, e.g., U.S. Pat. No. 3,610,795, which is incorporated by reference herein in its entirety.

The efficacy of treating or preventing *Chlamydia* infection by the methods of the present invention can be determined by detecting a clinical improvement as indicated by a change in the subject's symptoms and/or clinical parameters, as would be well known to one of skill in the art.

The pharmaceutical compositions of this invention include those suitable for oral, intranasal, rectal, topical, inhalation (e.g., via an aerosol) buccal (e.g., sub-lingual), vaginal (e.g., vaginal ring), rectal, intraurethral, parenteral (e.g., subcutaneous, intramuscular, intradermal, intraarticular, intrapleural, intraperitoneal, intracerebral, intraarterial, or intravenous), topical (i.e., both skin and mucosal surfaces, including but not limited to vaginal, urethral, rectal, labial, respiratory, oral, nasal, airway surfaces, etc.) and transdermal administration. The compositions herein can also be administered via a skin scarification method or transdermally via a patch, liquid or gel. The compositions can be delivered subdermally in the form of a biodegradable material that releases the compositions over time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In certain embodiments the compositions of this invention can be administered to the mucous membranes of a subject (e.g., via intravaginal administration). The formulations may be conveniently prepared in unit dosage form and may be prepared by any of the methods well known in the art. For example, formulations may be administered to the mucosa as a liquid, spray, ointment, gel and/or mist.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically and pharmaceutically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, Pharmaceutical Research 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year or as necessary to control the condition. In some embodiments, one, two, three or four doses over the lifetime of a subject can be adequate to achieve the desired therapeutic effect. In some embodiments, alternate day dosing can be employed (e.g., every other day). The amount and frequency of administration of the composition of this invention will vary depending on the particular condition being treated or to be prevented and the desired therapeutic effect.

In additional embodiments of this invention, the compositions of this invention can comprise a protein and/or immunogenic fragment and/or epitope thereof of a different pathogenic organism in any combination [e.g., a pathogenic organism that is sexually transmitted, including but not limited to: *Trichomonas* (e.g., *Trichomonas vaginalis*); a pathogenic yeast or fungus (e.g., *Candida albicans*), *Neisseria* (e.g., *N. gonorrhea*), *Treponema pallidum*, and pathogenic viruses (e.g., herpes simplex virus (HSV), human immunodeficiency virus (HIV), human papilloma virus (HPV)].

In some embodiments, the *Chlamydia* cell of this invention can be used as a vector to deliver a heterologous nucleotide sequence or heterologous nucleic acid molecule to a subject. The terms "heterologous nucleotide sequence" and "heterologous nucleic acid molecule" are used interchangeably herein and refer to a sequence that is not naturally produced in the cell or is not naturally produced or present in the cell in the configuration or orientation in which it is present in the cell as a heterologous sequence. For example, a heterologous nucleotide sequence may encode a protein that is naturally made by the cell, but the heterologous nucleotide sequence is present in the cell in a configuration that differs from the nucleotide sequence that is naturally present in the cell (e.g., the heterologous nucleotide sequence may be operably linked to a promoter and/or regulatory element(s) that are not naturally present in the cell or are not naturally present in the cell in the same configuration). In some embodiments, the heterologous nucleic acid can comprises an open reading frame that encodes a polypeptide or nontranslated RNA of interest (e.g., for delivery to a subject for a therapeutic effect).

As used herein, the term "vector" refers to a cell of this invention that functions as a nucleic acid delivery vehicle, and which comprises a heterologous nucleic acid molecule to be delivered.

In some embodiments, molecules that can introduced into a subject via a *Chlamydia* cell of this invention include heterologous DNA, RNA, polypeptides, small organic molecules, metals, or any combinations thereof.

In some embodiments, therapeutically useful molecules can be associated with the outside of the *Chlamydia* cell for transfer of the molecules into a subject. Such associated molecules can include DNA, RNA, small organic molecules, metals, carbohydrates, lipids and/or polypeptides. In one embodiment of the invention the therapeutically useful molecule is covalently linked (i.e., conjugated or chemically coupled) to the surface of the *Chlamydia* cell. Methods of covalently linking molecules are known by those skilled in the art.

The *Chlamydia* cells of the invention also find use in raising antibodies against a heterologous protein produced by a heterologous nucleic acid molecule and exposed on the cell surface. As a further alternative, an exogenous amino acid sequence may be attached to or inserted into the cell surface for antigen presentation to a cell, e.g., for administration to a subject to produce an immune response to the heterologous amino acid sequence.

In representative embodiments, a heterologous amino acid sequence can be attached to the surface of the *Chlamydia* cell of this invention that functions as a targeting sequence to target the *Chlamydia* cell to certain cells or tissues. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be used as a targeting sequence.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC I glycoproteins, carbohydrate components found on membrane glycoproteins, including, mannose, N-acetyl-galactosamine, N-acetylglucosamine, fucose, galactose, and the like.

As yet a further alternative, the targeting sequence may be a peptide that can be used for chemical coupling (e.g., can comprise arginine and/or lysine residues that can be chemically coupled through their R groups) to another molecule that targets entry into a cell.

The foregoing embodiments of the invention can be used to deliver a heterologous nucleic acid to a cell or subject as described herein. For example, the *Chlamydia* cell of this invention can be used to treat a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase) as described herein.

Any heterologous nucleic acid molecule(s) of interest may be delivered in the cells of the present invention. Nucleic acid molecules of interest include nucleic acids encoding polypeptides, including therapeutic (e.g., for medical or veterinary uses) or immunogenic (e.g., for vaccines) polypeptides.

In particular embodiments, the heterologous nucleic acid molecule of this invention encodes a protein or peptide or epitope of a pathogenic organism that is sexually transmitted, including but not limited to *Trichomonas* (e.g., *Trichomonas vaginalis*); a pathogenic yeast or fungus (e.g., *Candida albicans*), *Neisseria* (e.g., *N. gonorrhea*), *Treponema pallidum*, and pathogenic viruses (e.g., herpes simplex virus (HSV), human immunodeficiency virus (HIV), human papilloma virus (HPV), and any combination thereof.

Therapeutic polypeptides include, but are not limited to, cystic fibrosis transmembrane regulator protein (CFTR), dystrophin (including mini- and micro-dystrophins, see, e.g., Vincent et al., (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor −3 and −4, brain-derived neurotrophic factor, bone morphogenic proteins [including RANKL and VEGF], glial derived growth factor, transforming growth factor −α and −β, and the like), lysosomal acid α-glucosidase, α-galactosidase A, receptors (e.g., the tumor necrosis growth factorα soluble receptor), S100A1, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof.

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacal Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a vector of the invention.

The vector of this invention may also comprise a heterologous nucleic acid molecule that shares homology with and recombines with a locus on a chromosome in the subject to which the vector is administered. This approach can be utilized, for example, to correct a genetic defect in a cell in the subject.

The present invention also provides vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope gp160 protein, gp41, gp120), the HIV or SIV matrix/capsid proteins, and the HIV or SIV gag, pol and env gene products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (Immunity 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.*, 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

It will be understood by those skilled in the art that the heterologous nucleic acid molecule(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid molecule(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The vectors of this invention are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (α1-antitrypsin), Lesch-Nyhan Syndrome (hypoxanthine guanine phosphoribosyl transferase), Niemann-Pick disease (sphingomyelinase), Tay Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARK ct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, vectors according to the present invention permit the treatment and/or prevention of genetic diseases.

The vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, vectors according to the instant invention find use in diagnostic and screening methods, whereby a nucleic acid molecule of interest is transiently or stably expressed in a cell culture system, or alternatively, a transgenic animal model.

The vectors of the present invention can also be used for various non-therapeutic purposes, including but not limited to use in protocols to assess gene targeting, clearance, transcription, translation, etc., as would be apparent to one skilled in the art. The vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the vectors of the present invention may be used to produce an immune response in a subject. According to this embodiment, a vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

The vector comprising the heterologous nucleic acid is introduced into the subject, where the heterologous nucleic acid molecule encoding the immunogen can be expressed and induce an immune response in the subject against the immunogen.

The vectors of the present invention can also be administered for cancer immunotherapy by administration of a vector comprising a heterologous nucleic acid molecule encoding one or more cancer cell antigens (or an immunologically similar molecule) or any other immunogen that produces an immune response against a cancer cell. To illustrate, an immune response can be produced against a cancer cell antigen in a subject by administering a vector comprising a heterologous nucleic acid encoding the cancer cell antigen, for example to treat a patient with cancer and/or to prevent cancer from developing in the subject. Alternatively, the cancer antigen can be present on the surface of the *Chlamydia* cell or be otherwise associated with the cell.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the vector.

Cytokines may be administered by any method known in the art. Exogenous cytokines may be administered to the subject, or alternatively, a nucleic acid encoding a cytokine may be delivered to the subject using a vector, and the cytokine produced in vivo.

In some embodiments, the vector is administered to a subject to elicit an immunogenic response against an immunogenic polypeptide encoded by a heterologous nucleotide sequence in the vector cell. Typically, a quantity of cells producing an immunogenically effective amount of the polypeptide in combination with a pharmaceutically acceptable carrier is administered. An "immunogenically effective amount" is an amount of the immunogenic polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

The vectors of the invention can further be administered to elicit an immunogenic response (e.g., as a vaccine). Typically, immunogenic compositions of the present invention comprise an immunogenically effective amount of vector in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof.

In particular embodiments, more than one administration (e.g., two, three, four or more administrations) may be employed to achieve the desired level of immune response over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain).

Administration can also be to a tumor (e.g., in or near a tumor or a lymph node). The most suitable route in any given case will depend on the nature and severity of the condition being treated and/or prevented and on the nature of the particular vector that is being used.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a vector of the invention to a mammalian subject, wherein the vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1 and fragments thereof (e.g., I1C), S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the vector of the invention in a local rather than systemic manner, for example, in a depot or sustained-release formulation. Further, the vector can be delivered adhered to a surgically implantable matrix (e.g., as described in U.S. Patent Publication No. US-2004-0013645-A1).

The vectors disclosed herein can be administered to the lungs of a subject by any suitable means, optionally by administering an aerosol suspension of respirable particles comprised of the vectors, which the subject inhales. The respirable particles can be liquid or solid. Aerosols of liquid particles comprising the vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the vectors may likewise be produced with any solid particulate medicament aerosol generator, by techniques known in the pharmaceutical art.

The vectors can be administered to tissues of the CNS (e.g., brain, eye) and may advantageously result in broader distribution of the vector than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulimia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the vector is administered to the CNS (e.g., to the brain or to the eye). The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The vector may also be administered to different regions of the eye such as the retina, cornea and/or optic nerve.

The vector may be delivered into the cerebrospinal fluid (e.g., by lumbar puncture) for more disperse administration of the delivery vector. The vector may further be administered intravascularly to the CNS in situations in which the blood-brain barrier has been perturbed (e.g., brain tumor or cerebral infarct).

The vector can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the vector is administered in a liquid formulation by direct injection (e.g., stereotactic injection) to the desired region or compartment in the CNS. In other embodiments, the vector may be provided by topical application to the desired region or by intra-nasal administration of an aerosol formulation. Administration to the eye, may be by topical application of liquid droplets. As a further alternative, the vector may be administered as a solid, slow-release formulation (see, e.g., U.S. Pat. No. 7,201, 898).

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1. In Vitro Passage Selects for *Chlamydia muridarum* with Enhanced Infectivity in Cultured Cells but Attenuated Pathogenicity in Mouse Upper Genital Tract Although modern *Chlamydia muridarum* has been passaged for decades, there are no reports on the consequences of serial passage with a strong selection pressure to its fitness. In order to explore the potential for Pasteurian selection to induce genomic and phenotypic perturbations to *C. muridarum*, a starter population was passaged in cultured cells for 28 generations without standard infection assistance. The resultant population, designated CMG28, displays markedly reduced in vitro dependence on centrifugation for infection and lower incidence and severity of upper genital tract pathology following intravaginal inoculation into mice compared to the parental *C. muridarum*, CMG0. Deep sequencing of CMG0 and CMG28 revealed novel protein variants in the hypothetical genes TC0237 (Q117E) and TC0668 (G322R). In vitro attachment assays of isogenic plaque clone pairs with either mutations in TC0237 and TC0668 or only TC0237 reveal that TC0237 Q117E is solely responsible for an enhanced adherence to host cells. Paradoxically, double mutants, but not TC0237 Q117E single mutants, display severely attenuated in vivo pathogenicity. These findings implicate TC0237 and TC0668 as novel genetic factors involved in chlamydial attachment and pathogenicity, respectively, and show that serial passage under a selection pressure remains an effective tool for studying *Chlamydia* pathogenicity.

Infection with *Chlamydia trachomatis* in the lower genital tract of women can lead to upper genital tract inflammatory pathologies, such as hydrosalpinx, resulting in complications including ectopic pregnancy and infertility. Hydrosalpinx that is detectable by laparoscopic examination has been used as a surrogate marker for tubal factor infertility in women. However, the mechanisms by which *C. trachomatis* induces hydrosalpinges remain unknown. The murine pathogen *C. muridarum*, although not known to cause human diseases, has been extensively used for studying the mechanisms of *C. trachomatis* pathogenesis and immunity. This is primarily due to the ease of intravaginal infection of mice with *C. muridarum* organisms and their ability to induce hydrosalpinx in the oviduct, leading to mouse infertility.

Both *C. trachomatis* and *C. muridarum* share a highly conserved biphasic growth cycle, which begins with the attachment of an infectious elementary body (EB) to a host cell. Multiple putative chlamydial factors such as the major outer membrane protein (MOMP), the outer membrane complex protein B (OmcB) and the polymorphic membrane proteins (Pmps) and host-derived factors such as heparin sulfate, epidermal growth factor receptor (EGFR), estrogen receptor and insulin-like growth factor 2 receptor have been proposed to mediate chlamydial interactions with the host cells. However, the precise structural basis of the interactions between an EB and a host cell during chlamydial infection in animals and humans remains ill defined. Following the attachment to epithelial cells, *Chlamydiae* have been shown to induce endocytosis for aiding their own entry into host cells through the release of effectors, such as the Translocated Actin Recruiting Protein (TARP and CT694. The internalized EB then differentiates into a non-infectious but metabolically active reticulate body (RB) that is capable of multiplying within a cytoplasmic vacuole, termed an inclusion. To infect new cells, the progeny RBs must differentiate back to infectious EBs that then exit the infected cells. Stimulation of host cells with EBs, chlamydial proteins, and the intracellular RB replication in cultured cells can lead to the production of inflammatory cytokines and inflammatory cytokines are also frequently detected in *Chlamydia*-infected genital tract tissues. However, it remains unknown which and how chlamydial proteins contribute to pathogenicity in the genital tracts of animals and humans.

Frameshift mutations in the 360aa hypothetical ORF CT135 of highly passaged *C. trachomatis* serovar D have been identified to be responsible for varying degrees of infectivity in mouse genital tract. One mutant, isolated 49 days after intravaginal infection of the parental population, acquired a "T" deletion in the $45^{th}$ codon resulting in premature termination at the $60^{th}$ codon. These organisms reproducibly exhibit lower genital tract shedding for infections in excess of eight weeks, garnering the strain name "Late Clearance" (D-LC). An opposing mutant isolated 10 days after infection carries a "T" insertion at the $182^{nd}$ codon, terminates at the $194^{th}$ codon, and can be cleared from the lower genital tract in less than 4 weeks, giving it the name "Early Clearance" (D-EC). These findings demonstrate that phenotype-altering mutations can accumulate in genomes of passaged *Chlamydia*. Although analogous mutations have been discovered in TC0412, the *C. muridarum* homologue of CT135, it is not known whether these mutations also affect *C. muridarum* infectivity and pathogenicity in the mouse genital tract.

We have previously shown that both adequate ascension of infection to the upper genital tract and activation of an appropriate tubal inflammatory response are required for the induction of hydrosalpinx. Defining the virulence factors that contribute to either ascending infection or tubal inflammation has been a priority in *Chlamydia* research. Recent advances in transforming *Chlamydia* and inducing mutations have provided useful tools for investigating pathogenic mechanisms. However, these approaches either rely on prior discovery of virulence factors encoded on the plasmid and chromosome or functional assays to screen mutant libraries for phenotypes. Serial cell culture passage, an alternative functional assay, has been employed to select for chromosomal mutants of *C. trachomatis* serovars E and L2; however, this study lacked a novel selection pressure since these strains were historically maintained with the same in vitro conditions used during passage. Antibiotic resistance adaptations, on the other hand, have successfully been revealed through in vitro selection pressure. Despite these advances and prior attempts, no chlamydial genetic factors have been directly associated with the ability of the organism to induce upper genital tract pathology.

In this study, we sought to determine whether *Chlamydia* can be genetically adapted to an atypical niche, thereby decreasing its pathogenic fitness in vivo. Though this strategy, classically defined as Pasteurian selection, has generated numerous live attenuated microbial vaccines in the past, it has not been applied to *Chlamydia*, which lacks an approved vaccine. To achieve attenuation, *C. muridarum* was serially passaged in vitro to functionally select for organisms with enhanced infectivity towards cultured host cells. Parental and passaged organisms contain multiple pre-existing mutations in TC0412, but the hypothetical ORFs TC0237 and TC0668 acquired novel mutations during passage. The mutation in TC0237 can be solely attributed to an in vitro attachment enhancement phenotype, while TC0237 and TC0668 double mutants, but not TC0237 alone, display severely attenuated in vivo pathogenicity. Unlike CT135, lesions in TC0412 failed to impact either the in vitro attachment or in vivo pathogenicity of the organism. In light of these findings, we propose that TC0237 is a regulator of host adherence and postulate that TC0668 is a significant chlamydial virulence factor.

Chlamydial Organism Growth and In Vitro Passage

*Chlamydia muridarum* (CM) strain Nigg organisms were propagated and purified in HeLa cells (human cervical carcinoma epithelial cells, ATCC cat # CCL2). Prior to *C.*

*muridarum* infection, host cells were grown in either 24- or 6-well tissue culture plates or tissue culture flasks in DMEM (GIBCO BRL, Rockville, Md.) supplemented with 10% fetal bovine serum (FBS; GIBCO BRL) (D10) at 37° C. in an incubator supplied with 5% $CO_2$ (standard incubation conditions). For assisted infections, host cell cultures were pre-incubated with 30 μg/mL DEAE-Dextran (Sigma-Aldrich, St. Louis, Mo.) in DMEM for 15 min, aspirated to remove the DEAE solution, inoculated with *C. muridarum* diluted in sucrose-phosphate-glutamate (SPG; 218 mM sucrose, 3.76 mM $KH_2PO_4$, 7.1 mM $K_2HPO_4$, 4.9 mM glutamate, pH 7.2), and centrifuged at 500 RCF and room temperature (RT) for 1 h to maximize infection. For unassisted infections, host cell cultures were inoculated with *C. muridarum* diluted in SPG and incubated for 2 h with manual rotating every 15 min to selectively infect organisms with enhanced attachment to and/or entry into host cells. Following infection, inoculums were aspirated, replaced by D10 supplemented with 2 μg/mL of cycloheximide (Sigma-Aldrich Co., St Luis, Mo.) to make host cells stationary, and incubated for 24 h before being processed.

For in vitro passage, 6-well plates with HeLa cell monolayers were initially infected under unassisted infection conditions described above with purified parental *C. muridarum* EBs, designated CMG0, diluted to an MOI of 0.5 in a 1 mL inoculum. After incubating for 24 h, the progeny *C. muridarum* organisms, designated passage generation 1 or CMG1, were harvested and infected on fresh HeLa cell monolayers with assisted infection conditions described above to form passage generation 2, or CMG2. This alternating unassisted/assisted infection cycle was repeated until CMG28 was reached. As a general rule, odd passage generations represent the result of an unassisted infection and even an assisted infection passage.

Plaque-Forming Assay and Genotyping

A plaque-forming assay was used to isolate individual clones from both CMG0 and CMG28. Briefly, purified EBs were inoculated onto confluent monolayers of McCoy cells in 6-well tissue culture plates and treated with assisted infection conditions described above. The inoculum was then removed and replaced with agarose overlay medium (1× Dulbecco's modified Eagle's medium, 10% fetal bovine serum, 0.2 μg/mL cycloheximide, and 1% of agarose). The cells were then incubated for five days to allow plaques to form. Plaques were then picked into SPG and a portion of the plaque stock used to PCR amplify and Sanger sequence (ABI, Life Technologies, Grand Island, N.Y. 14072) the coding regions of chromosomal ORFs TC0237, TC0412, and TC0668. Based on the three gene sequence results, selected clones were re-plaqued to ensure monoclonality before large-scale amplification, whole genome sequencing, and subsequent experiments.

Sequencing and Analysis of *C. muridarum* Genomes

Genomic DNA from CMG0 and CMG28 populations and their plaqued-purified clones were subjected to deep sequencing using the Illumina HiSeq2000 platform (UTHSCSA Greehey Children's Cancer Research Institute (GCCRI) Genome Sequencing Facility). Briefly, purified DNA was fragmented by Covaris 5220 Ultra Sonicator and DNA-Seq library was prepared using the TruSeq DNA Sample Preparation kit (Illumina, Inc.) according to the manufacturer's protocol. DNA-Seq libraries were sequenced with a 50 bp single-end sequencing module on the Illumina HiSeq2000 platform. After demultiplexing with CASAVA, sequence reads and associated qualities were exported in FASTQ format. All reads were deposited to the National Center for Biotechnology Information (NCBI) Sequence Read Archive (SRA) with run accessions of SRR1531377 for CMG0, SRR1531380 for CMG28, SRR1736634 for CMG0.1.1, SRR1736639 for CMG0.10.1, SRR1531430 for CMG0.21.3, SRR1736644 for CMG28.12.3, SRR1737027 for CMG28.38.1, and SRR1736648 for CMG28.54.1.

Reads in FASTQ format were mapped to the *Chlamydia muridarum* strain Nigg reference chromosome (NC_002620.2) and pMoPn plasmid (NC_02182.1) using the Burrows-Wheeler Aligner mem algorithm [PMID: 19451168]. The resulting SAM file was converted to BAM format and sorted with Samtools [PMID: 19505943]. Insertions and deletions (indels) in the mapped reads were realigned using the Genome Analysis Toolkit [PMID: 21478889]. A multisample pileup of the processed BAMs for CMG0, CMG28 and CMG0.21.3 was generated by Samtools and pipelined into VarScan [PMID: 22300766] for detection and VCF output of variants with a minimum average base quality of Q20 and minimum read fraction of 0.05. Low frequency variants that share read fractions between the two populations and clonal control (CMG0.21.3) were ruled as sequencing errors, while shared consensus variants against the Nigg reference were determined from the parental strain, CMG0. All other high quality variants were mapped to genes and their protein consequences predicted with the MathWorks MATLAB r2014a Bioinformatics Toolbox and GenBank annotations for the accessions listed above. The only variants discovered in passaged organisms lie within the ORFs of TC0237, TC0412, and TC0668, with the remaining genome unaffected.

Based on both the whole genome sequencing and the targeted gene sequencing results, three pairs of plaqued-purified isogenic clones together with CMG0 and CMG28 population organisms were selected for subsequent phenotype analyses. Select genomes were uploaded to GenBank with accessions CP009760.1 for the CMG0 parental consensus, CP009608.1 for CMG0.1.1, and CP009609.1 for CMG28.38.1, each being a representative of the population from which they originate.

Centrifugation Dependence and Attachment Assays

*C. muridarum* populations and plaque-purified clones were titrated for number of inclusion-forming units (IFU) per mL with the assisted and unassisted infection conditions described above, but without prior incubation with DEAE-Dextran, in order to compare dependence on centrifugation for infection. Briefly, purified *C. muridarum* EBs were serially diluted in SPG before being inoculated onto confluent HeLa monolayers grown on glass coverslips in 24-well tissue culture plates. The assisted infection conditions were modified to include 1 h pre-incubation under standard incubation conditions before centrifugation in order to equal the total of 2 h incubation required for unassisted infections. Monolayers were fixed and processed for immunofluorescence detection of *C. muridarum* inclusions following 24 h of growth. The genome copy of each organism stock per mL was also quantitated using qPCR.

The attachment and entry efficiency of the *C. muridarum* organism were further compared via direct observation. Briefly, purified EBs were diluted in SPG and inoculated onto the HeLa cell monolayers grown on coverslips in 24-well tissue culture plates at 4° C. for 1 h. After a brief wash with chilled DMEM to remove unbound EBs, one set of the coverslips was processed for immunofluorescence detection of cell-associated EBs while 1 mL pre-warmed D10 was added to the remaining cultures and incubated at 37° C. At different time points after incubation, a set of coverslips was processed for detecting chlamydial organisms inside the host cells. Intense fluorescent particles, inclusions, and host cells were counted under the same view across five random views of the coverslip and averaged. The results are expressed as number of C. muridarum particles or inclusions per host cell.

Mouse Infection and Live Organism Recovery from Vaginal Swabs and Genital Tract Tissues Purified C. muridarum EBs were used to infect six to seven week-old female C3H/HeJ mice (Jackson Laboratories, Inc., Bar Harbor, Me.) intravaginally with $2 \times 10^5$ inclusion-forming units (IFUs) in 20 μL of SPG. Five days prior to infection, each mouse was injected with 2.5 mg medroxyprogesterone (Depo-Provera; Pharmacia Upjohn, Kalamazoo, Mich.) subcutaneously to increase mouse susceptibility to infection. After infection, mice were monitored for vaginal live organism shedding and sacrificed on different days post-infection (as indicated in individual experiments) for quantitating live organisms recovered from different segments of the genital tract and/or for observing gross genital tract pathologies.

For monitoring live organism shedding from swab samples, vaginal/cervical swabs were taken every three to four days for the first week and weekly thereafter until negative shedding was observed for two consecutive time points. To quantitate live chlamydial organisms, each swab was soaked in 0.5 mL of SPG, vortexed with glass beads, and the chlamydial organisms released into the supernatant were titrated on HeLa cell monolayers in duplicate. The infected cultures were processed for immunofluorescence assay as described below. Inclusions were counted in five random fields per coverslip under a fluorescence microscope. For coverslips with less than one IFU per field, entire coverslips were counted. Coverslips showing obvious cytotoxicity of HeLa cells were excluded. The total number of IFUs per swab was calculated based on the mean IFUs per view, the ratio of the view area to that of the well, dilution factor, and inoculation volumes. Where possible, a mean IFU/swab was derived from the serially diluted and duplicate samples for any given swab. The total number of IFUs/swab was converted into $\log_{10}$ and used to calculate the mean and standard deviation across mice of the same group at each time point.

To monitor ascending infection, mice infected in parallel experiments were sacrificed on day 14 after infection. Whole genital tracts were sterilely harvested and each tract was divided into three portions including vagina/cervix (VC), uterus/uterine horn (UH) and oviduct/ovary (OV). VC was defined as the lower genital tract (LGT) while both UH & OV as the upper genital tract (UGT). Tissue segments were homogenized in 0.2 mL cold SPG using a 2 mL tissue grinder (cat # K885300-0002, Fisher scientific, Pittsburgh, Pa.). After a brief sonication and centrifugation at 3000 rpm for 5 min to pellet large debris, the supernatants were titrated for live C. muridarum organisms on HeLa cells as described above. The results were expressed as $\log_{10}$ IFUs per tissue segment.

Mouse Genital Tract Pathology Evaluation

Mice were sacrificed 60 days after infection to evaluate urogenital tract tissue pathology. Before removing the genital tract tissues from the mice, an in situ gross examination was performed under a stereoscope (Olympus, Center Valley, Pa.) for evidence of hydrosalpinx formation and any other gross abnormalities. The genital tract tissues were then excised in their entirety from the vagina to the ovary and laid on a blue photography mat for acquisition of digital images. The oviduct hydrosalpinges were visually scored based on their dilation size using a scoring system as described previously. No oviduct dilation or swelling found with a stereoscope inspection was defined as no hydrosalpinx and assigned a score of zero (0); hydrosalpinx was only visible after amplification (1); hydrosalpinx is clearly visible with the naked eye but the size is smaller than that of ovary (2); The size of hydrosalpinx is similar to that of ovary (3); or larger than ovary (4). Both the incidence and severity scores of oviduct hydrosalpinx were analyzed for statistical differences between groups of mice.

For histological scoring and inflammatory cell counting, the excised mouse genital tract tissues, after photographing, were fixed in 10% neutral formalin, embedded in paraffin, and serially sectioned longitudinally at 5 μm widths. Efforts were made to include cervix, uterine horns, oviducts, and lumenal structures of each tissue in each section. The sections were stained with hematoxylin and eosin (H&E). The H&E stained sections were scored for severity of inflammation and oviduct dilation based on the modified schemes established previously by researchers who were blind to mouse group designation. Scores from both sides of the oviducts were added to represent the oviduct pathology for a given mouse, and the individual mouse scores were calculated into medians for each group.

Inflammatory cell infiltrates were scored for oviduct tissue: 0, no significant infiltration; 1, infiltration at a single focus; 2, infiltration at two to four foci; 3, infiltration at more than four foci; and 4, confluent infiltration. Scoring for dilatation of oviduct was as follows: 0, no significant dilatation; 1, mild dilation of a single cross section; 2, one to three dilated cross sections (the largest diameter is smaller than that of the ovary on the same side); 3, more than three dilated cross sections (the largest diameter is equal to that of the ovary on the same side); and 4, confluent pronounced dilation (the largest diameter is larger than that of the ovary on the same side).

Immunofluorescence Assay

HeLa cells grown on coverslips were fixed with 4% (w/v) paraformaldehyde (Sigma) dissolved in PBS for 30 min at room temperature, followed by permeabilization with 2% (w/v) saponin (Sigma) for an additional 30 min. After washing and blocking, the cell samples were subjected to antibody and chemical staining. Hoechst 33342 (Sigma) was used to visualize DNA. A rabbit anti-chlamydial organism antibody, raised by immunization with purified C. muridarum elementary bodies, plus a goat anti-rabbit IgG secondary antibody conjugated with Cy2 (green; Jackson ImmunoResearch Laboratories, Inc., West Grove, Pa.) were used to visualize chlamydial organism-containing inclusions. Immunofluorescence images were acquired using an Olympus AX-70 fluorescence microscope equipped with multiple filter sets and Simple PCI imaging software (Olympus). The images were processed using the Adobe Photoshop program (Adobe Systems, San Jose, Calif.). For titrating the live organisms recovered from a given sample, the mean number of inclusions per view was derived from counting five random views. The total number of live organisms in a given sample was calculated based on the mean inclusions per view, ratio of view area to that of the well, dilution factor, and inoculum volume and expressed as $\log_{10}$ IFUs per sample.

Multiplex Array for Profiling Cytokines in Oviduct Tissue

Oviduct/ovary tissues were harvested from mice infected with CMG0 (n=5) or CMG28 (n=5) on day 14 after intravaginal inoculation with C. muridarum for generating homogenates. The homogenates were used for simultaneous measurements of 32 mouse cytokines [23 plex group I (cat # M60-009RDPD) plus 9 plex group II (MD0-00000EL)]

using a multiplex bead array assay (Bio-Plex 200 System, all from Bio-Rad, Hercules, Calif. 94547) by following the manufacturer's instruction. All cytokines are expressed in mean pg/mL plus/minus standard deviation. The means from the two mouse groups infected with CMG0 or CMG28 were used for calculating ratio and statistics analysis.

Statistics Analyses

Quantitative data including number of live organisms (IFUs), IFU ratios, and number of organisms or IFUs per cell were analyzed using Student's t-test or Kruskal-Wallis. Cytokine levels were first subjected to an f-test to determine whether the variance of each group is significantly different ($p<0.05$) followed by the appropriate t-test (two-sample with either equal or unequal variance). Qualitative data, including incidence rates, were analyzed using Fisher's exact test. Semi-quantitative data, including gross and microscopic pathology scores, were analyzed using the Wilcoxon rank sum test.

In Vitro Passage Selects for Chlamydia muridarum with Mutations in Chromosomal Genes TC0237 and TC0668

C. muridarum organisms were passed in HeLa cell culture for 28 generations as described in the Materials and Methods section to generate CMG28 organisms. We compared the genomes of CMG28 organisms against the original C. muridarum organisms without passage (CMG0). First, next generation sequencing (NGS) of the CMG0 and CMG28 populations and a combination of various bioinformatics tools were used to screen for mutations that were either introduced or affected by passage. Most regions of CMG28 genomes were found to be identical to those of CMG0, except for the introduction of novel protein variants in two chromosomal genes: a consensus Q117E substitution in ORF TC0237 and a subconsensus G322R substitution in TC0668. Interestingly, many mutations in TC0412 were detected in both CMG0 and CMG28 genomes although no novel TC0412 variants were found in CMG28 compared to CMG0.

We then picked plaques from the CMG0 and CMG28 populations and sequenced their chromosomal regions coding for TC0237, TC0412, and TC0668 using traditional Sanger sequencing. As predicted by NGS, CMG28 clones carry the TC0237(Q117E) mutation while none of CMG0 clones do (Table 1). It is likely that TC0412 mutations had accumulated during decades of in vitro maintenance of our C. muridarum stock, as was found for CT135 of C. trachomatis serovar D. For this study, we focus on three TC0412 lesions with similarity to the D-LC and D-EC disruptions of CT135, as well as an intermediate mutation that lies between them. These TC0412 variants include a −84 T (T insertion at $84^{th}$ ORF nucleotide position) frameshift similar to the D-LC disruption, a G262T nonsense intermediate disruption, and a −435 T frameshift similar to the D-EC disruption. All three lesions are predicted to terminate the ORF at or shortly after its position like in D-LC and D-EC.

To correlate the opposing genotypes of TC0237, TC0412, and TC0668 with phenotypes, we selected three pairs of isogenic clones to characterize alongside the original CMG0 and CMG28 populations. These six isogenic clones were twice plaque-purified and subjected to deep whole genome sequencing to ensure monoclonality. As shown in Table 1, each of the three pairs possessed a unique TC0412 mutation and within each pair, the two clones differed in TC0237 and/or TC0668 genotypes. For example, both CMG0.1.1 and CMG28.38.1 have the TC0412 −435 T frameshift but CMG28.38.1 additionally carries the TC0237(Q117E) mutation. The rest of the genomes and plasmids of the two clones are identical. The remaining two CMG28-derived clone pairs have TC0412 −84 T frameshift and G262T nonsense mutations and both TC0237(Q117E) and TC0668(G322R) mutations. We were unable to isolate plaques with the TC0668 mutation only as the consensus TC0237(Q117E) mutation is always present in CMG28-derived clones.

TC0237(Q117E) Mutants are More Efficient in Attaching to Cultured Cells

As shown in Table 2, three pairs of isogenic clones along with their original CMG0 and CMG28 populations were compared for their in vitro growth in HeLa cells. Each of these eight organisms was amplified, purified, and titrated for both genome copies and live organisms per stock volume. Live organism titration was carried out using both DEAF-Dextran pretreatment of HeLa cells and centrifugation of the infected cultures, which maximizes the in vitro growth of the C. muridarum organisms. Indeed, the IFU titers obtained under these maximally assisted infection conditions, were closer to the genome copy numbers of the corresponding organisms. We then re-titrated the eight organisms under two infection conditions: with or without centrifugation. No DEAE-Dextran was used under either condition to prevent confounding charge-related effects. Interestingly, all CMG28 organisms reached significantly higher titers than CMG0 organisms when titrated without centrifugation. Since the untreated, non-centrifuged condition was similar to conditions used in alternating cycles during the in vitro passaging, the above observation suggests that the CMG28 organisms were likely selected to be more efficient for infecting HeLa cells in the absence of any assisted infection conditions. When titrated with versus without centrifugation the titers of CMG0 plaques increased dramatically at 19- to 31-fold compared to the consistent 5-fold increase of CMG28 organisms. These findings suggest that CMG28 organisms adapted to invade HeLa cells more efficiently in the absence of centrifugation.

Though CMG28 organisms display a reduced dependence on centrifugation for infection, these results do not distinguish between more efficient attachment or intracellular growth. To address this question, we compared the attachment efficiency of CMG0 and CMG28 populations and clones on HeLa cell monolayers under unassisted infection conditions (FIG. 1). After the organisms were allowed to attach to HeLa cells for 1 h at 4° C., cell samples were rinsed with cold medium three times to remove loosely-associated or free-floating EBs and fixed for detecting the cell-associated chlamydial particles. We found that even after the number of live input organisms was standardized across both organisms, the number of chlamydial particles associated with each cell was significantly higher in cultures inoculated with the CMG28 population and its clones than those of CMG0. When the parallel cultures were incubated for another 6 h at 37° C., the number of intracellular chlamydial organisms per cell continued to be significantly higher in cultures inoculated with CMG28 than CMG0. This trend continued when observed for inclusions inside each cell at 22 h after infection. These observations suggest that the CMG28 organisms are more efficient in attaching to HeLa cells during infection in the absence of centrifugation and the enhanced attachment results in more productive infection.

Although their TC0412 and TC0668 genotypes vary, all CMG28-derived clones carry the TC0237(Q117E) mutation. These organisms independently displayed significantly enhanced attachment to HeLa cells compared to their corresponding CMG0 control population or isogenic clones, which strongly suggests that the TC0237(Q117E) mutation is responsible for the enhanced attachment to cultured cells.

Figure 2:
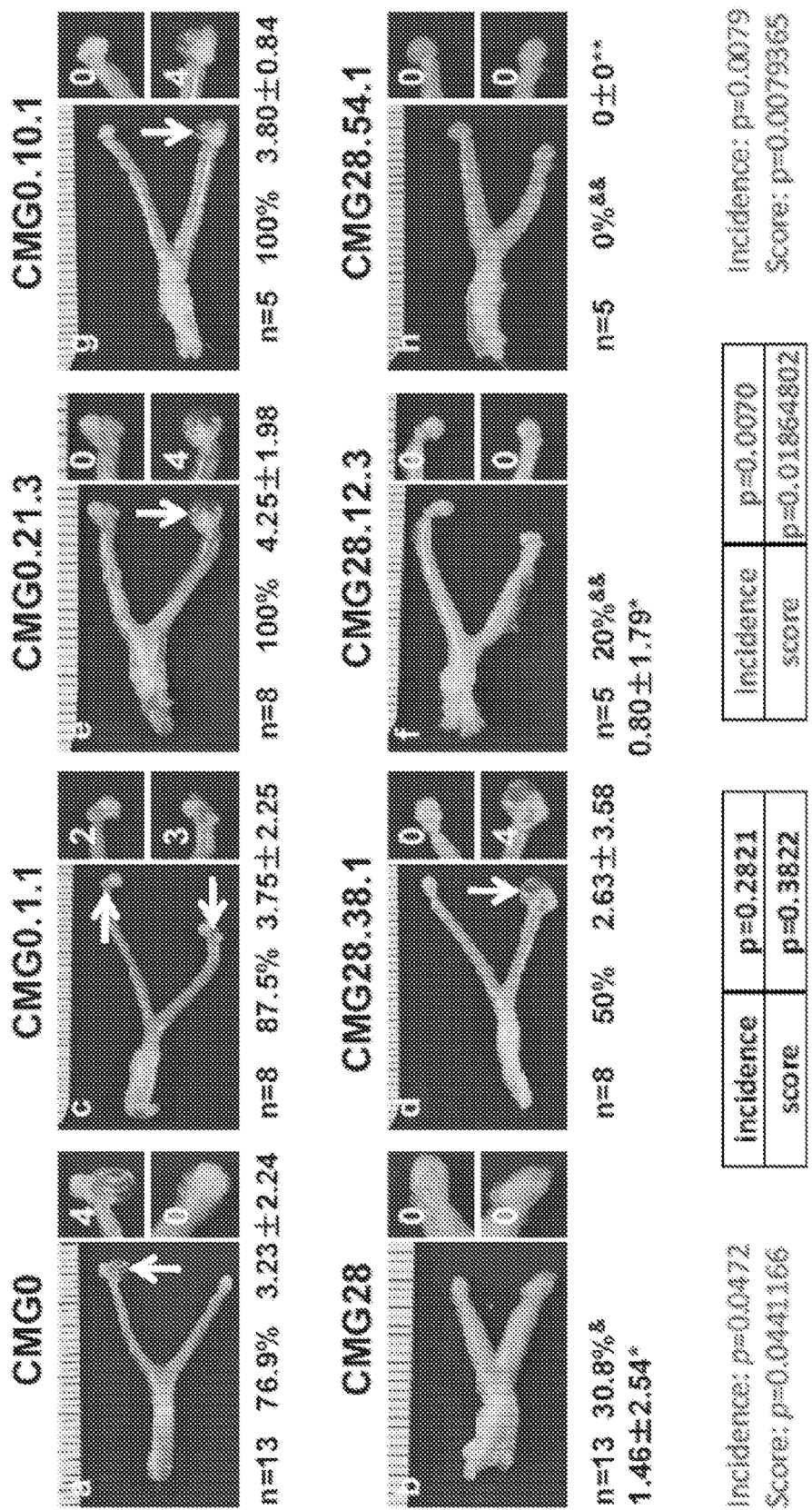
FIG. 2. Induction of hydrosalpinx in mice by the CMG0 and CMG28 populations and plaque-purified clones. C3H/Hej mice were intravaginally infected with $2\times10^5$ IFUs of the following 8 *C. muridarum* respectively, including the CMG0 (panel a) and CMG28 (b) population pair (n=13/group) and three plaque-purified isogenic clone pairs CMG0.1.1 (c, n=8) versus CMG28.38.1 (d, n=8), CMG0.21.3 (e, n=8) versus CMG28.12.3 (f, n=5) and CMG0.10.1 (g, n=5) versus CMG28.54.1 (h, n=5). The mice were sacrificed 60 days after infection for observing hydrosalpinx. One representative whole genital tract image from each group of mice was presented in the left columns with an orientation of vagina on the left and oviduct/ovary on the right sides. The areas covering the oviduct/ovary portions were magnified and shown on the right of the corresponding whole genital tract images. Hydrosalpinges are indicated by white arrows and hydrosalpinx severity scores by white numbers. The hydrosalpinx incidence rates and severity scores are listed under the corresponding images. Mice with hydrosalpinx in either or both oviducts were considered positive for hydrosalpinx. The severity of both hydrosalpinges from a given mouse was scored separately and added together as the severity score assigned to the particular mouse. Fisher's exact test was used for comparing incidence rates (&, p<0.05 and &&, p<0.01) while Wilcoxon rank-sum test was used for severity scores (*, p<0.05 and **, p<0.01) between the CMG0 and CMG28 organisms. Note that all CMG28 organisms induced more significant hydrosalpinges than their CMG0 counterparts with the exception of the CMG0.1.1 and CMG28.38.1 pair.
Figure 3:
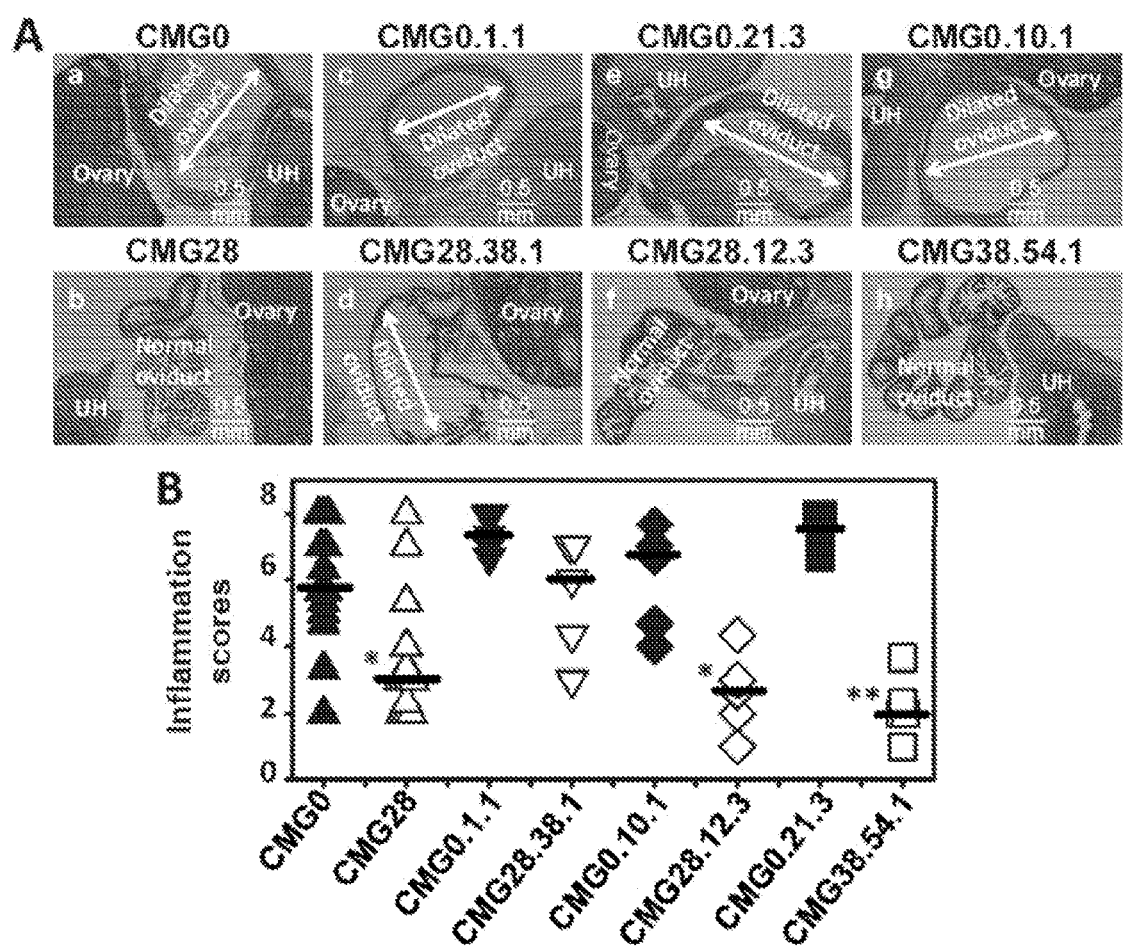
Figure 4:
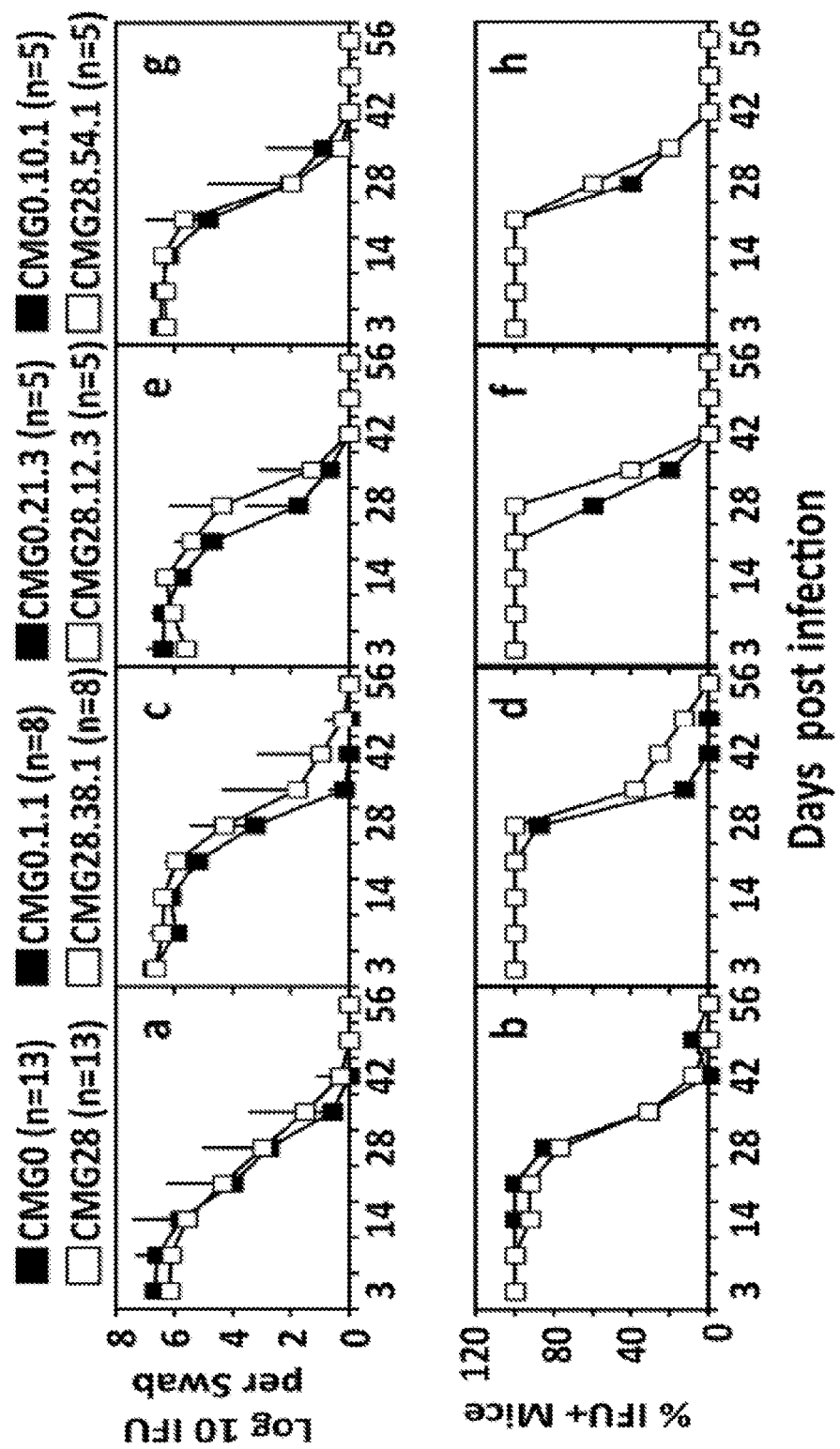
Figure 5:
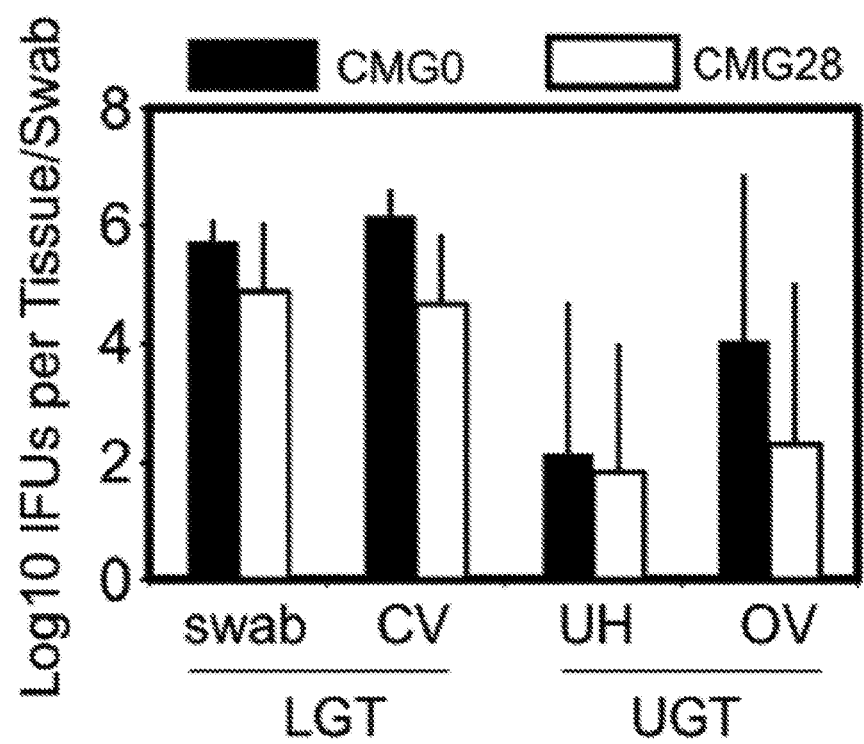
Figure 6:
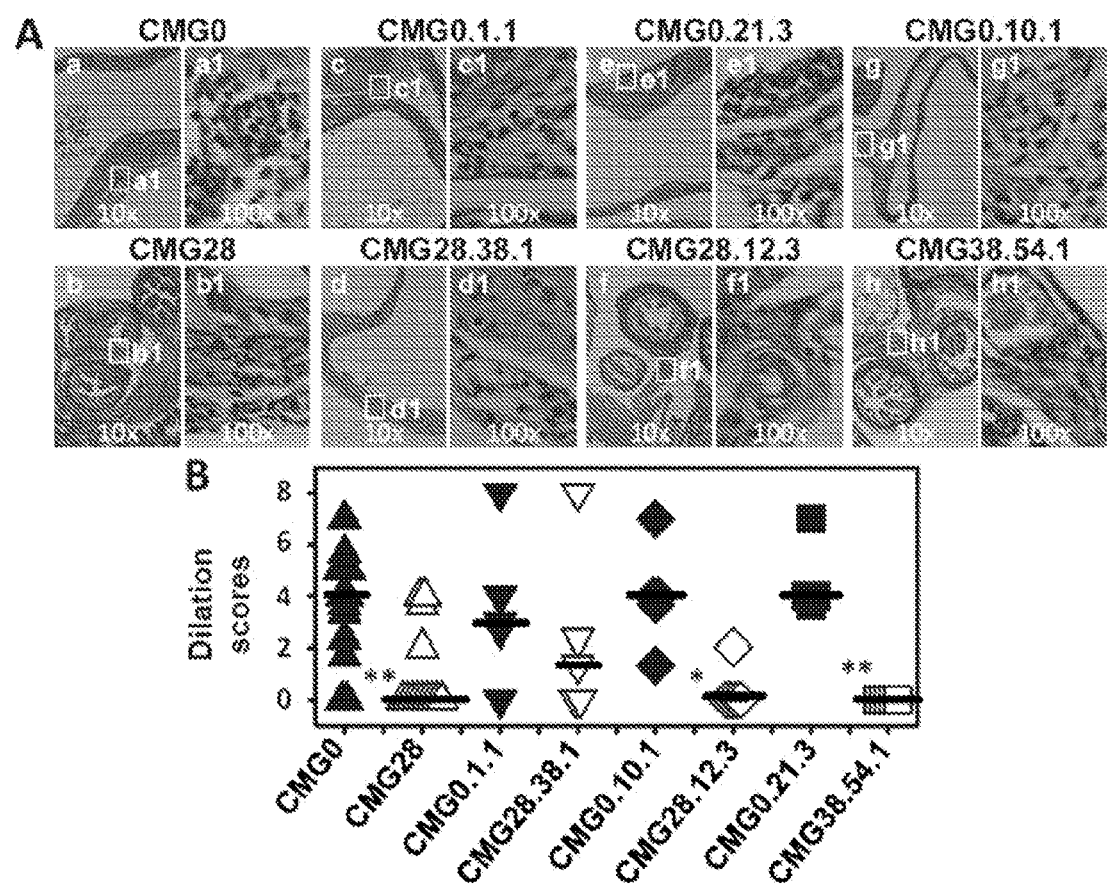

TC0668(G322R) Mutants are Significantly Attenuated in Inducing Hydrosalpinx in Mice Following in vitro characterization of CMG0 and CMG28 organisms, we evaluated their pathogenicity in the mouse upper genital tract. When oviduct tissues were examined on day 60 after intravaginal infection with $2 \times 10^5$ IFUs of each of the eight CMG0 or CMG28 organisms (FIG. 2), we found that all mice infected with CMG0 organisms developed significant upper genital tract pathology with hydrosalpinx incidence rates of 76.9% or higher and severity scores of $3.23 \pm 2.24$ or more. However, CMG28 organisms, with exception of CMG28.38.1 without the TC0668(G322R) mutation, induced significantly reduced levels of hydrosalpinx with an incidence rate of 30.8% or less and severity scores of less than 1.5. Although the CMG28.38.1 clone also showed reduced pathogenicity, the attenuation was not as significant since this clone induced 50% mice to develop hydrosalpinx with a mean severity score of 2.63. Thus, the attenuation of pathogenicity seemed to correlate with the presence of the TC0668(G322R) mutation. The attenuated pathogenicity by the CMG28 population and CMG28 clones was also confirmed by microscopy, which showed a significantly reduced oviduct lumenal dilation in mice infected with TC0668(G322R) mutants (FIG. 3).

CMG28 Organisms are as Infectious as the CMG0 Organisms in the Mouse Genital Tract Following intravaginal infection with either CMG0 or CMG28 populations or clones as described above, mice were monitored for live organism shedding from the lower genital tract at different time points (FIG. 4). We found that both the number of live organisms recovered and percent of mice remaining positive for shedding live organisms at each time point were similar regardless of the chlamydial organisms used for infection. This observation suggests that both the CMG0 and CMG28 populations and clones maintain similar levels of infectivity in mouse lower genital tract. Unlike CT135, ORF disruptions at sites analogous to D-LC and D-EC within TC0412 have no obvious effect on shedding.

To further compare the ascending infection between the CMG0 and CMG28 population organisms, we monitored live organism recovery from genital tract tissues harvested from mice on day 14 after infection (FIG. 5). There was no significant difference in the number of live organisms recovered between mice infected with CMG0 or CMG28 population organisms. There was also no significant difference in *Chlamydia* load detected in either the lower and upper genital tracts, including cervix/vagina (CV), uterus/uterine horn (UH) and oviduct/ovary (OV) tissues. It appears that both CMG0 and CMG28 organisms comparably ascended to and replicate in the upper genital tract of mice. Although the above observation was made on a single day and with the CMG0 and CMG28 populations, we can still conclude that these two types of organisms share similar growth patterns in the mouse genital tract since live organisms from the lower and upper genital tract tissues were surveyed in relation to one another.

CMG28 Organisms are Less Inflammatory in the Mouse Upper Genital Tract

Oviduct tissues collected on day 60 after infection were evaluated for inflammatory cell histopathology under a microscope. As shown in FIG. 6, the inflammatory infiltration was significantly reduced in mice infected with the CMG28 population. In order to dissect the immunological mechanisms behind attenuation of CMG28 organisms, we compared the cytokine levels in oviduct tissue homogenates harvested on day 14 from mice infected with CMG0 or CMG28 populations (Table 3) and found that 12 out of the 32 cytokines measured were significantly higher in mice infected with CMG0 than CMG28. The remaining cytokines were either not detected in CMG0 or CMG28 homogenates or were not significantly different. The 12 cytokines with decreased concentrations in CMG28-infected mice include: pro-inflammatory cytokines IL-1α and IL-1β; Th1-promoting cytokines IL-12 and IL-15; Th2 cytokines IL-10 and eotaxin; Th17 cytokine IL-17; chemokines MIP-1α, MIG, and MIP-2; as well as growth factor VEGF. It is clear from these observations that the CMG28 organisms are attenuated in inducing inflammation in mouse oviducts despite adequate ascension to the upper genital tract.

In the current study, we have used the traditional Pasteurian approach of in vitro passage selection to attenuate pathogenicity in vivo in order to identify chlamydial factors relevant to chlamydial pathogenicity. For every other infection cycle, the chlamydial organisms were applied to cell monolayers without assistance in the form of DEAE-Dextran pre-incubation and centrifugation. This infection cycle selects for chlamydial organisms with enhanced affinity to HeLa cells. The successful organisms were then amplified via an assisted infection cycle. Alternating selection cycles were repeated 28 times, which has allowed us to obtain the CMG28 organisms with mutations accumulating in the regions coding for ORFs TC0237 and TC0668. These genotypes were confirmed by Sanger sequencing of plaque-isolated clones and re-sequencing the whole genomes of three pairs of isogenic clones.

Following passage, characterization of three pairs of isogenic plaque-purified clones along with the CMG0 and CMG28 populations revealed that all CMG28 organisms developed an enhanced attachment to cultured cells. Since TC0237(Q117E) is the only mutation shared by all the CMG28 organisms, this mutation is likely responsible for the in vitro attachment enhancement phenotype. This conclusion is supported by the fact that CMG28.38.1 carrying only the TC0237(Q117E) mutation with a wild type TC0668 also displayed the enhanced attachment phenotype. On the contrary, when evaluated in mice, all CMG28 organisms except for the CMG28.38.1 clone were highly attenuated in inducing hydrosalpinx. The attenuated pathogenicity correlates with the presence of the TC0668(G322R) mutation.

It is worth noting that no plaque clones with a wild type, or annotated, TC0412 ORF sequence, were recovered from the CMG0 and CMG28 populations. TC0412 encodes a conserved 365 AA hypothetical protein, although no putative conserved domains have been detected. It shares ~60% AA sequence identity with its homolog CT135 from *C. trachomatis* serovar D and weaker homology (~20% AA identity) with its homologs in other chlamydial species. Both TC0412 and CT135 are predicted to contain four trans-membrane domains. The TC0412 mutants characterized in this study are highly analogous to those previously discovered in CT135, implicating common selective pressures to disrupt the ORF. However, neither the CT135-associated delayed clearance (D-LC) or early clearance (D-EC) phenotypes could be replicated by these TC0412 analogs. TC0412 mutants also did not differ in their ability to attach to cultured HeLa cells and failed to affect the pathogenicity of *C. muridarum* in the mouse upper genital tract. Thus, it is unlikely that TC0412 is irrelevant to murine urogenital tract infection, but it is still possible that CT135 is necessary for pathogenesis in the human urogenital tract.

The two ORFs that accumulated mutations during 28 cell culture passages encode two hypothetical proteins that are both conserved and unique to *Chlamydiae*. TC0237, found on the complementary strand of the *C. muridarum* strain Nigg reference genome, codes for a 159 amino acid (AA) protein with no known function. On the other hand, TC0237 contains a domain of unknown function 720 (DUF720) motif, which is also found in its neighboring ORFs TC0236 (coding for a 172AA hypothetical protein) and TC0235 (170AA hypothetical protein). These three sequential proteins are paralogous to each other and are predicted to be encoded in an operon. TC0237, TC0236, and TC0235 are all highly conserved within the *Chlamydiae* and *Chlamydophila* genera, an example of such being ~90% AA sequence identity with their *C. trachomatis* serovar D homologs CT849, CT848, and CT847. Since we have correlated a Q117E mutation in TC0237 with enhanced attachment to cultured cells, it is possible that this cluster of the three proteins may participate in initial chlamydial interactions with host cells. However, we found that the TC0237(Q117E) mutation may not participate in the pathogenicity of *C. muridarum* in mice. This hypothesis originates from the observation that CMG28.38.1 with only the TC0237 (Q117E) mutation was as effective as its isogenic background strain, CMG0.1.1, in inducing hydrosalpinx following intravaginal infection.

TC0668 encodes a highly conserved hypothetical protein with 408 AA and contains a single DUF1207 domain. It shares ~90% AA identity with its homologue CT389 from *C. trachomatis* serovar D and its first 24 AA residues are predicted to constitute a gram positive/negative signal sequence. In addition, the region covering residues 360-380 of CT389 has weak homology with mammalian phosphatase signatures, suggesting that TC0668 may be a secreted phosphatase. Partially consistent with this prediction and analyses, CT389 was enriched in outer membrane complex (OMC) fraction of *C. trachomatis*, suggesting it is associated with the OMC. It appears that the selective advantage of TC0668(G322R) for adaptation to unassisted in vitro infection is less than that of TC0237(Q117E) given that TC0668(G322R) is found at a subconsensus and TC0237 (Q117E) at a consensus population level in CMG28. Although we have not been able to isolate clones that carry the TC0668 mutation alone due to the fact that all CMG28 clones carry the TC0237(Q117E) mutation, the available data has allowed us to associate TC0668 mutation with the attenuation of in vivo pathogenicity by *C. muridarum*. However, it is unknown whether TC0668 is solely responsible for pathogenicity or if TC0668 and TC0237 act synergistically to induce upper genital tract disease.

In summary, this study has revealed that TC0237 is involved in the chlamydial host attachment process, TC0668 is associated with upper genital tract pathogenesis of *C. muridarum*, and *Chlamydia* is tractable to Pasteurian passage and selection.

Figure 7:
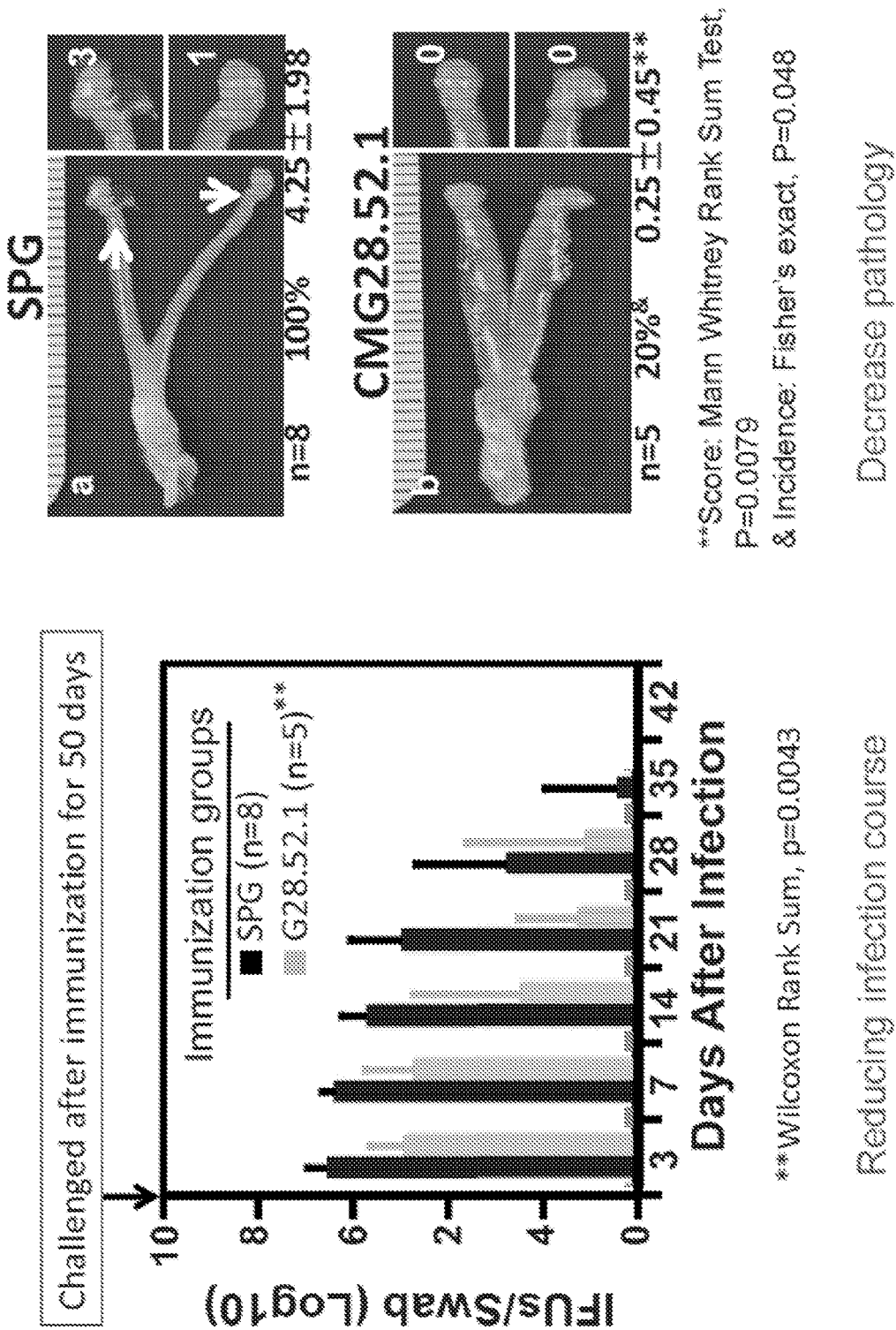

Example 2. Immunization of C3H/HeJ Mice with Attenuated G28.52.1 Induces Protection Against Wild Type *C. muridarum* (G0.1.1) Infection and Pathology FIG. 7 shows the results of experiments carried out as described, demonstrating reducing infection course over time and decreased pathology.

Figure 8:
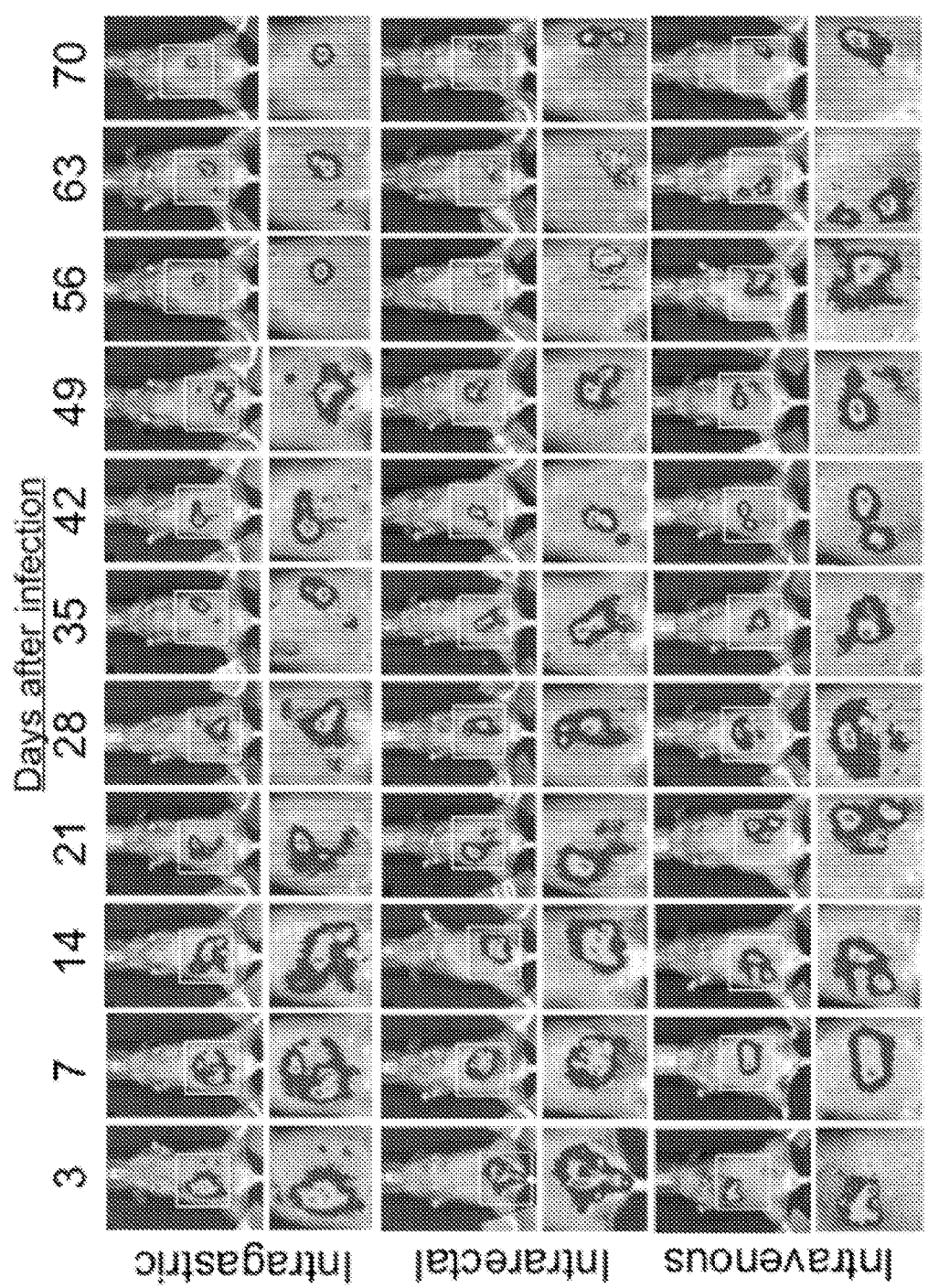

Example 3. In Vivo and Ex Vivo Imaging Reveals a Long-Lasting Chlamydial Infection in the Mouse Gastrointestinal Tract Following Genital Tract Inoculation Intravaginal infection with *Chlamydia muridarum* in mice can ascend to the upper genital tract resulting in hydrosalpinx, a pathological hallmark for tubal infertility in women infected with *C. trachomatis*. In the present study, we utilized in vivo imaging of *C. muridarum* infection in mice following an intravaginal inoculation and confirmed rapid ascent of the chlamydial organisms from the lower to upper genital tracts. Unexpectedly, the *C. muridarum*-derived signal was still detectable in the abdominal area 100 days after inoculation. Ex vivo imaging of the mouse organs revealed that the long-lasting presence of the chlamydial signal was restricted to the gastrointestinal (GI) tract, which was validated by directly measuring the chlamydial live organisms and genomes in the same organs. The *C. muridarum* spreading from the genital to the GI tracts was detected in different mouse strains and appeared to be independent of oral or rectal routes. Mice prevented from orally taking up excretions also developed the long-lasting GI tract infection. Inoculation of *C. muridarum* directly into the upper genital tract, which resulted in a delayed vaginal shedding of live organisms, accelerated the chlamydial spreading to the GI tract. Thus, we have demonstrated that the genital tract chlamydial organisms may use a systemic route to spread to and establish a long-lasting infection in the GI tract (see FIG. 8).

The foregoing is illustrative of the present invention, and is not to be construed as limiting thereof. The invention is defined by the following claims, with equivalents of the claims to be included therein.

TABLE 1

| Chromosomal Variant | Affected Gene | length (codons) | Nucleotide mutation | Protein mutation | Chlamydia muridarum clones | | | | | |
|---|---|---|---|---|---|---|---|---|---|---|
| | | | | | CMG0. 10.1 | CMG28. 54.1 | CMG0. 21.3 | CMG28. 12.3 | CMG0. 1.1 | CMG28. 38.1 |
| G 277313 C | TC0237 | 160 | G 349 C | Q 117 E | − | + | − | + | − | + |
| — 472842 T | TC0412 | 366 | — 84 T | fs29 | + | + | − | − | − | − |
| G 473020 T | TC0412 | 366 | G 262 T | E 88 * | − | − | + | + | − | − |
| — 473193 T | TC0412 | 366 | — 435 T | fs146 | − | − | − | − | + | + |
| G 797979 A | TC0668 | 409 | G 964 A | G 322 R | − | + | − | + | − | − |

Genotypes of *C. muridarum* organisms characterized in the current study. Isogenic clones were selected by pairing parental control genomes from CMG0 with TC0237(Q117E) single or TC0237(Q117E) and TC0668(G322R) double mutants from CMG28. Aside from carrying either one or both of the mutations in TC0237 and TC0668, isogenic pairs differ from one another by their unique TC0412 genotype. Chromosomal variants numbered according to the parent CMG0 consensus chromosome sequence.

"fs" represents a frameshift mutation beginning at the indicated codon.

"−" signifies lack of genotype while "+" indicates the clone carries the genotype.

TABLE 2

In vitro growth properties of the CMG0 and CMG28 population and plaque-purified clone organisms.

| Organisms | Genome copies/ml | Infection condition | IFUs/ml | Ratio | G0 vs. G28 |
|---|---|---|---|---|---|
| CMG0 | 2.50E+10 | DE + Centri | 9.00E+09 | | |
| | | Centri | 7.03E+09 ± 1.56E+09 | 43.56 | 0.0115 |
| | | No treat | 1.61E+08 ± 2.22E+07 | | |
| CMG28 | 6.75E+10 | DE + Centri | 2.70E+10 | | |
| | | Centri | 2.20E+10 ± 8.79E+09 | 5.80 | |
| | | No treat | 3.79E+09 ± 2.27E+09 | | |
| CMG0.1.1 | 9.43E+10 | DE + Centri | 4.01E+10 | | |
| | | Centri | 2.41E+10 ± 5.98E+09 | 18.87 | 0.0159 |
| | | No treat | 1.28E+09 ± 7.56E+08 | | |
| CMG28.38.1 | 4.71E+10 | DE + Centri | 2.35E+10 | | |
| | | Centri | 1.48E+10 ± 3.57E+09 | 4.87 | |
| | | No treat | 3.68E+09 ± 1.86E+09 | | |
| CMG0.21.3 | 9.26E+09 | DE + Centri | 4.30E+09 | | |
| | | Centri | 4.29E+09 ± 6.47E+08 | 31.04 | 0.0088 |
| | | No treat | 1.38E+08 ± 4.99E+07 | | |
| CMG28.12.3 | 2.74E+10 | DE + Centri | 1.33E+10 | | |
| | | Centri | 1.24E+10 ± 1.68E+09 | 5.11 | |
| | | No treat | 2.43E+09 ± 4.25E+08 | | |
| CMG0.10.1 | 2.67E+10 | DE + Centri | 1.02E+10 | | |
| | | Centri | 5.20E+09 ± 1.11E+09 | 20.70 | 0.0168 |
| | | No treat | 2.51E+08 ± 6.31E+07 | | |
| CMG28.54.1 | 6.03E+10 | DE + Centri | 4.63E+10 | | |
| | | Centri | 4.33E+10 ± 5.03E+09 | 5.23 | |
| | | No treat | 8.28E+09 ± 4.10E+09 | | |

*C. muridarum* organisms, as listed in the first column, were amplified and purified.
Each of the eight purified stock organisms was quantitated for genome copies per mL using qPCR ($2^{nd}$ column) and titrated for number of live organisms under three different infection conditions ($3^{rd}$ column) including DEAE treatment plus centrifugation (DE + Centri), centrifugation alone (Centri) and no treatment (No treat).
The live organisms were expressed as inclusion forming units (IFUs) per mL ($4^{th}$ column).
The ratios of IFUs titrated from centrifugation versus no treatment conditions were calculated for each organism ($5^{th}$ column) and the ratios were compared between the CMG0 and CMG28 organisms within each pair (final column).
The ratios from the CMG0 organisms were significantly higher than those from the CMG28 organisms.

TABLE 3

Cytokines from oviduct tissues of mice infected with *C. muridarum* CMG0 or CMG28.

| Strain | CMG0 (n = 5) | CMG28 (n = 5) | CMG0/CMG28 | P value |
|---|---|---|---|---|
| IL-1α | 3809.7 ± 2847.6 | 38.2 ± 41.7 | 99.67 | p < 0.05 |
| IL-1β | 6248.2 ± 4272.9 | 122.4 ± 178.1 | 51.05 | p < 0.05 |
| IL-2 | 7.1 ± 7.8 | 0 | | |
| IL-3 | 5.8 ± 3.5 | 1.7 ± 1.2 | 3.53 | |
| IL-4 | 15.6 ± 10.4 | 2.0 ± 2.3 | 7.89 | |
| IL-5 | 0 | 0 | | |
| IL-6 | 267.1 ± 294.7 | 10.3 ± 12.6 | 25.97 | |
| IL-9 | 304.7 ± 121.4 | 166.0 ± 53.7 | 1.84 | |
| IL-10 | 41.3 ± 27.1 | 6.2 ± 5.0 | 6.70 | p < 0.05 |
| IL-12 (p40) | 312.8 ± 196.9 | 61.2 ± 52.0 | 5.11 | p < 0.05 |
| IL-12 (p70) | 123.0 ± 83.6 | 7.2 ± 6.6 | 17.03 | p < 0.05 |
| IL-13 | 971.4 ± 553.4 | 400.5 ± 154.2 | 2.43 | |
| IL-17 | 73.8 ± 50.2 | 4.3 ± 6.2 | 17.07 | p < 0.05 |
| Eotaxin | 1506.2 ± 1029.3 | 105.4 ± 124.6 | 14.28 | p < 0.05 |
| G-CSF | 12420.0 ± 10815.5 | 1552.7 ± 944.3 | 8.00 | |
| GM-CSF | 92.9 ± 62.2 | 24.3 ± 28.1 | 3.83 | |
| IFNγ | 147.1 ± 121.0 | 21.7 ± 23.5 | 6.76 | |
| MCP-1 | 3891.9 ± 3282.3 | 1356.5 ± 1558.4 | 2.87 | |
| MIP-1α | 922.4 ± 681.3 | 69.6 ± 77.6 | 13.24 | p < 0.05 |
| MIP-1β | 221.9 ± 171.3 | 42.0 ± 35.0 | 5.28 | |
| RANTES | 946.6 ± 770.2 | 224.3 ± 233.6 | 4.22 | |
| TNFα | 163.6 ± 131.3 | 16.9 ± 16.2 | 9.71 | |
| IL-15 | 347.7 ± 233.4 | 18.8 ± 22.0 | 18.46 | p < 0.05 |
| KC | 498.6 ± 386.0 | 56.1 ± 57.2 | 8.89 | |
| IL-18 | 111.5 ± 103.7 | 0 | | |
| FGF-basic | 1131.0 ± 536.9 | 703.4 ± 102.6 | 1.61 | |
| LIF | 234.9 ± 203.3 | 11.7 ± 12.9 | 20.03 | |
| M-CSF | 360.9 ± 236.9 | 76.5 ± 44.8 | 4.72 | |
| MIG | 68208.3 ± 45450.3 | 7556.5 ± 9488.6 | 9.03 | p < 0.05 |
| MIP-2 | 12745.6 ± 8969.6 | 43.4 ± 60.9 | 293.90 | p < 0.05 |
| PDGF-BB | 0 | 0 | | |
| VEGF | 9355.2 ± 5326.1 | 1668.7 ± 595.6 | 5.61 | p < 0.05 |

Table 3. Cytokines from oviduct tissues of mice infected with the CMG0 or CMG28 population organisms.
Oviduct tissue homogenates were produced from mice infected with CMG0 (n = 5) or CMG28 (n = 5) on day 14 after intravaginal inoculation for simultaneous measurement of 32 cytokines using a multiplex bead array assay.
All cytokines are expressed in pg/mL as mean plus/minus standard deviation.
The means from the two organism strains were used for calculating ratio and Student's t-test.
P values under 0.05 are listed in the last column and the corresponding ratios of CMG0 versus CMG28 are highlighted in bold face.

TABLE 4

| Amino Acid Residue | Three-Letter Code | One-Letter Code |
|---|---|---|
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |

TABLE 4-continued

| Amino Acid Residue | Abbreviation | |
|---|---|---|
| | Three-Letter Code | One-Letter Code |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 5

| Modified Amino Acid Residue Amino Acid Residue Derivatives | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

```
Mutations in corresponding genes of Chlamydia muridarum and Chlamydia trachomatis
TC0237       1    MSAPIPPAKDSKYVSALPPLEPLRTPPMAELLFGIYSLLLEAVEIRQQTV  50
                  |||......|::|||:|||||||.|||:|||||.||||||||||||||:|:
CT849        1    MSAATSQIGDTQYVSSLPPLEPLGTPPIAELLFSIYSLLLEAVEIRQETI  50

TC0237_001   51   LTQSQQLNDNTNIQQQLNQETNRIKYAVVNAGAKEDEITRVQNQNQNYSA  100
                  ||||:||||||||||||||||||:||||||.:||||||||||||||||||
OCT849_001   51   LTQSKQLNDNTNIQQQLNQETNQIKYAVVGSGAKEDEITRVQNQNQNYSA  100

TC0237_001   101  QRSNIQDQLVTARQNGQIILSHASTNINIMQQIAQMNSSFIKTLNSVGST  150
                  |||||||||||||||||||||||||||||||||||.|||||||||||||
OCT849_001   101  QRSNIQDQLVTARQNGQIILSHASTNINIMQQIAQQNSSFIKTLNSVGST  150

TC0237_001   151  VNQLNKPLS*                                          160
                  |||||||||
OCT849_01    151  VNQLNKPLS*                                          160

TC0237 (Q117E) (C. muridarum): CT849 (Q117E) (C. trachomatis). Amino acid
sequence of TC0237 is SEQ ID NO: 4. Amino acid sequence of CT849 is SEQ ID NO: 1.
TC0668       1    MMEPLRFGYFFCILFIGLLQTVFAKEPDSCPDCKNNWKEVTHTDQLPENI  50
                  ||:|||||||||.::...|||..|||||:|||||:|||||||||||||||
CT389        1    MMKPLRFGYFFCAIYFTLLQAAFAKEPNSCPDCQNNWKEVTHTDQLPENI  50

EMBOSS_001   51   IHADDACYHSGYVQALIDMHFLDSCCQVIVEDQTAYLFSLPQDDVTRNAI  100
                  ||||||||||||||||||||||||||||||:|||||||||.|||||||
EMBOSS_001   51   IHADDACYHSGYVQALIDMHFLDSCCQVIVENQTAYLFSLPTDDVTRNAI  100

EMBOSS_001   101  INLIKDLPFIQSVEICQASYQTCHHQGPYGKSSLPEQRSFCTKVCGKEAI  150
                  |||||||||.||||||||||||||||||:||:||||||||||||||||
EMBOSS_001   101  INLIKDLPFIHSVEICQASYQTCHHQGPHGKTSLPEQRSFCTKVCGKEAI  150

EMBOSS_001   151  WLPQNTILFTPLVADPRQATNSAGIRFNDEVIGKRVGSAVFGGDFIFLRL  200
                  |||:|||||:||||||||||||||||||||:|||||||:|||||||||
EMBOSS_001   151  WLPWNTILFSPLVADPRQATNSAGIRFNDEVLGKRVGSATFGGDFIFLRL  200

EMBOSS_001   201  FDVSRFHGDMDIGLQGAVFSVFDLDNPDACMVNSDFFVSALLSFAVNKWS  250
                  ||:||||||||||||||||||||||:|||||||||||||:||..:||||||
EMBOSS_001   201  FDISRFHGDMDIGLQGAVFSVFDLDHPEACMVNSDFFVAALCNFAVNKWS  250
```

```
EMBOSS_001    251  YRLRLWHLSSHLGDEFILANQLPPGKRYNRSDEAVDFFASFRYTPQIRVY  300
                   ||.|||||||||||||||||||||.|||||||||||||||||||||||||
EMBOSS_001    251  YRFRLWHLSSHLGDEFILANQLPPKKRYNRSDEAVDFFASFRYTPQIRVY  300

EMBOSS_001    301  GGIGYIISRDLTFPEDPLYFEGGLELRPFGLREDNLHAQPIFAMHFRFWG  350
                   |||||||||||||||||||||||||:|||||||||||||||:||||||.
EMBOSS_001    301  GGIGYIISRDLTFPEDPLYFEGGIELRPFGLREDNLHAQPVFAMHFRFWE  350

EMBOSS_001    350  EHDFSIDQTYILGMEWSKFQDVGRKIRAVLEYHQGFSHEGQFVREECDYY  400
                   |||||||||||:||||||||||||:|||||||||||||||||||||||||
EMBOSS_001    350  EHDFSIDQTYIVGMEWSKFQDVGRKVRAVLEYHQGFSHEGQFVREECDYY  400

EMBOSS_001    401  GFRLSYGF*                                          409
                   ||||||||
EMBOSS_001    401  GFRLSYGF*                                          409
```

TC0668 (G322R) (*C. muridarum*): CT389 (G322r) (*C. trachomatis*). TC0668 (G216*) (*C. muridarum*): CT389 (G216*) (*C. trachomatis*). Amino acid sequence of TC01668 is SEQ ID NO: 5. Amino acid sequence of CT389 is SEQ IC NO: 2.

```
TC0412          1  MVSFDLSVTTTNIGAGYDDIQRMLNGVTCSSGGMGLLTPSACSPMSSFCS   50
                   ||||||:....|....|.:|.||||..||::||:|||||..||||.:||.
CT135           1  MVSFDLNDPVRNTDNHYRNINRMLNSATCAAGGIGLLTPVVCSPMGAFCF   50

EMBOSS_001     51  SNQPYSARDLKNRIHQFCQHSGPITGFYSLYNEKIMFEEALLVPTVLEAV  100
                   :...|.||.||.:||...|...|||..||||||.||:||||||  .||:|||||
EMBOSS_001     51  AQGPSSAEDLGHRIQHFVACSGPAAGFYSLSNERIMFEEA-AVPSVLEAV   99

EMBOSS_001    101  ESTFWISALSRLGGERPSTFDTVILSFFVGLISLVCGAMFVGIVSSAVKI  150
                   |:||||||.:||.|..|||.|||:::|...:|.||||||||||.|||.||||
EMBOSS_001    101  EATFWISAFARLRGNEPSTCDTVMMSCVIGCISLVCGAMFVAIVSCAVKI  149

EMBOSS_001    151  YRLMQTMRQARTLNENVQRLLQPQATNMRSAFAKLKGIVASKALDQVEQG  200
                   .|:::||..|.|..:.|..||.||.:|||||:|||||::||||:|.:||:||:|
EMBOSS_001    150  SRIVRTMTQAHALRETIQRQLAARATDMRSAYSKLKGIIAIRALNEVERG  199

EMBOSS_001    201  YRKFRNRMITSFVANALITIAFCALLASVILSAFFIGGASGCLMAAFFGC  250
                   :||.|:|:||:|||||||||:||||||||:::|||.|.||..|.::|||
EMBOSS_001    200  HRKLRNKMITAFVANALITLAFCALLASAVIAAFFFGAASAGLASVFFGC  249

EMBOSS_001    251  LGVGLGSLTIGMLVGIVSAICQRKHKQEAARCIQRGIFYSLILEQMQRFP  300
                   |...|:|.:|:||||||.||||.|.:.|||||||||...|:|:||||||
EMBOSS_001    250  LWGGIGALAVGVLVGIVSGICQRNYKVEAARCIQRGALYALVLEKMQRFP  299

EMBOSS_001    301  KDFFRDPVAKSIMAIQAGEALDEGKLSWKEMPSITACLGREGLDAQAYSF  350
                   |:|.:|.||||::||||||:|.|:|:|||:||||||||||||:|||||||
EMBOSS_001    300  KEFLKDGVAKSVVAIAQGESLDTGELAWEEMPSITACLGREGMDAQAYSF  349

EMBOSS_001    351  ISSSPLDGRIEEAFR*                                   366
                   :|:|||||.||.
EMBOSS_001    350  LSASPLDARIE*----                                   361
```

TC0412 (fs29, as a result of deletion of the 84th T) (*C. muridarum*) (SEQ ID NO: 6): proteoform? CT135 (fs29) (*C. trachomatis*)
TC0412 (E88*, as a result of G26T) (*C. muridarum*)(SEQ ID NO: 6): proteoform? CT135 (E88*) (*C. trachomatis*)
TC0412 (fs146, as a result of deletion of the 535th T) (*C. muridarum*) SEQ ID NO: 6): proteoform? CT135 (fs145) (*C. trachomatis*). Amino acid sequence of TC0412 is SEQ ID NO: 6. Amino acid sequence of CT135 is SEQ ID NO: 3.

---

What is claimed is:

1. An isolated *Chlamydia trachomatis* cell comprising:
   a) a substitution at Q117 in open reading frame CT849, wherein said amino acid numbering is based on the amino acid sequence of SEQ ID NO:1; and
   b) a G216* mutation in open reading frame CT389, wherein said amino acid numbering is based on the amino acid sequence of SEQ ID NO:2,
   wherein said *Chlamydia trachomatis* cell has a phenotype due to said substitution of (a) and said mutation of (b) of attenuated pathogenicity.

2. The isolated *Chlamydia trachomatis* cell of claim 1, wherein the substitution in open reading frame CT849 is Q117E.

3. The isolated *Chlamydia trachomatis* cell of claim 1, further comprising a substitution at G322 in open reading frame CT389.

4. The isolated *Chlamydia trachomatis* cell of claim 1, further comprising a mutation in the open reading frame CT135 selected from the group consisting of:
   a) a CT135fs29 mutation;
   b) a CT135E88* mutation;
   c) a CT135fs145 mutation; and
   d) any combination of (a) (c) above,
   wherein said amino acid numbering is based on the amino acid sequence of SEQ ID NO:3.

5. The isolated *Chlamydia trachomatis* cell of claim 1, further comprising a heterologous nucleic acid molecule.

6. A composition comprising the isolated *Chlamydia trachomatis* cell of claim 1 and a pharmaceutically acceptable carrier.

7. A composition comprising the isolated *Chlamydia trachomatis* cell of claim 5 and a pharmaceutically acceptable carrier.

8. The isolated Chlamydia trachomatis cell of claim 3, wherein the substitution at G322 in open reading frame CT389 is G322R.

* * * * *

UNITED STATES PATENT AND TRADEMARK OFFICE
CERTIFICATE OF CORRECTION

PATENT NO. : 10,596,247 B2
APPLICATION NO. : 15/551829
DATED : March 24, 2020
INVENTOR(S) : Guangming Zhong It is certified that error appears in the above-identified patent and that said Letters Patent is hereby corrected as shown below:

In the Specification

Column 23, Line 44:
Please correct "fatase], [β-galactosidase]" to read -- fatase], B [β-galactosidase] --

Signed and Sealed this
Twenty-seventh Day of October, 2020

Andrei Iancu
*Director of the United States Patent and Trademark Office*

SEQUENCE LISTING

<160> NUMBER OF SEQ ID NOS: 6

<210> SEQ ID NO 1
<211> LENGTH: 159
<212> TYPE: PRT
<213> ORGANISM: Chlamydia trachomatis

<400> SEQUENCE: 1

Met Ser Ala Ala Thr Ser Gln Ile Gly Asp Thr Gln Tyr Val Ser Ser
1               5                   10                  15

Leu Pro Leu Glu Pro Leu Gly Thr Pro Pro Ile Ala Glu Leu Leu
            20                  25                  30

Phe Ser Ile Tyr Ser Leu Leu Leu Glu Ala Val Glu Ile Arg Gln Glu

```
                35                  40                  45
Thr Ile Leu Thr Gln Ser Lys Gln Leu Asn Asp Asn Thr Asn Ile Gln
             50                  55                  60

Gln Gln Leu Asn Gln Glu Thr Asn Gln Ile Lys Tyr Ala Val Val Gly
 65                  70                  75                  80

Ser Gly Ala Lys Glu Asp Glu Ile Thr Arg Val Gln Asn Gln Asn Gln
                 85                  90                  95

Asn Tyr Ser Ala Gln Arg Ser Asn Ile Gln Asp Gln Leu Val Thr Ala
            100                 105                 110

Arg Gln Asn Gly Gln Ile Ile Leu Ser His Ala Ser Thr Asn Ile Asn
        115                 120                 125

Ile Met Gln Gln Ile Ala Gln Gln Asn Ser Ser Phe Ile Lys Thr Leu
    130                 135                 140

Asn Ser Val Gly Ser Thr Val Asn Gln Leu Asn Lys Pro Leu Ser
145                 150                 155

<210> SEQ ID NO 2
<211> LENGTH: 408
<212> TYPE: PRT
<213> ORGANISM: Chlamydia trachomatis

<400> SEQUENCE: 2

Met Met Lys Pro Leu Arg Phe Gly Tyr Phe Phe Cys Ala Ile Tyr Phe
  1               5                  10                  15

Thr Leu Leu Gln Ala Ala Phe Ala Lys Glu Pro Asn Ser Cys Pro Asp
             20                  25                  30

Cys Gln Asn Asn Trp Lys Glu Val Thr His Thr Asp Gln Leu Pro Glu
         35                  40                  45

Asn Ile Ile His Ala Asp Asp Ala Cys Tyr His Ser Gly Tyr Val Gln
     50                  55                  60

Ala Leu Ile Asp Met His Phe Leu Asp Ser Cys Cys Gln Val Ile Val
 65                  70                  75                  80

Glu Asn Gln Thr Ala Tyr Leu Phe Ser Leu Pro Thr Asp Asp Val Thr
                 85                  90                  95

Arg Asn Ala Ile Ile Asn Leu Ile Lys Asp Leu Pro Phe Ile His Ser
            100                 105                 110

Val Glu Ile Cys Gln Ala Ser Tyr Gln Thr Cys His His Gln Gly Pro
        115                 120                 125

His Gly Lys Thr Ser Leu Pro Glu Gln Arg Ser Phe Cys Thr Lys Val
    130                 135                 140

Cys Gly Lys Glu Ala Ile Trp Leu Pro Gln Asn Thr Ile Leu Phe Ser
145                 150                 155                 160

Pro Leu Val Ala Asp Pro Arg Gln Ala Thr Asn Ser Ala Gly Ile Arg
                165                 170                 175

Phe Asn Asp Glu Val Leu Gly Lys Arg Val Gly Ser Ala Thr Phe Gly
            180                 185                 190

Gly Asp Phe Ile Phe Leu Arg Leu Phe Asp Ile Ser Arg Phe His Gly
        195                 200                 205

Asp Met Asp Ile Gly Leu Gln Gly Ala Val Phe Ser Val Phe Asp Leu
    210                 215                 220

Asp His Pro Glu Ala Cys Met Val Asn Ser Asp Phe Phe Val Ala Ala
225                 230                 235                 240

Leu Cys Asn Phe Ala Val Asn Lys Trp Ser Tyr Arg Phe Arg Leu Trp
                245                 250                 255
```

```
His Leu Ser Ser His Leu Gly Asp Glu Phe Ile Leu Ala Asn Gln Leu
            260                 265                 270

Pro Pro Lys Lys Arg Tyr Asn Arg Ser Asp Glu Ala Val Asp Phe Phe
        275                 280                 285

Ala Ser Phe Arg Tyr Thr Pro Gln Ile Arg Val Tyr Gly Gly Ile Gly
    290                 295                 300

Tyr Ile Ile Ser Arg Asp Leu Thr Phe Pro Glu Asp Pro Leu Tyr Phe
305                 310                 315                 320

Glu Gly Gly Ile Glu Leu Arg Pro Phe Gly Leu Arg Glu Asp Asn Leu
            325                 330                 335

His Ala Gln Pro Val Phe Ala Met His Phe Arg Phe Trp Glu Glu His
        340                 345                 350

Asp Phe Ser Ile Asp Gln Thr Tyr Ile Val Gly Met Glu Trp Ser Lys
    355                 360                 365

Phe Gln Asp Val Gly Arg Lys Val Arg Ala Val Leu Glu Tyr His Gln
370                 375                 380

Gly Phe Ser His Glu Gly Gln Phe Val Arg Glu Cys Asp Tyr Tyr
385                 390                 395                 400

Gly Phe Arg Leu Ser Tyr Gly Phe
                405

<210> SEQ ID NO 3
<211> LENGTH: 360
<212> TYPE: PRT
<213> ORGANISM: Chlamydia trachomatis

<400> SEQUENCE: 3

Met Val Ser Phe Asp Leu Asn Asp Pro Val Arg Asn Thr Asp Asn His
1               5                   10                  15

Tyr Arg Asn Ile Asn Arg Met Leu Asn Ser Ala Thr Cys Ala Ala Gly
            20                  25                  30

Gly Ile Gly Leu Leu Thr Pro Val Val Cys Ser Pro Met Gly Ala Phe
        35                  40                  45

Cys Phe Ala Gln Gly Pro Ser Ser Ala Glu Asp Leu Gly His Arg Ile
    50                  55                  60

Gln His Phe Val Ala Cys Ser Gly Pro Ala Ala Gly Phe Tyr Ser Leu
65                  70                  75                  80

Ser Asn Glu Arg Ile Met Phe Glu Glu Ala Ala Val Pro Ser Val Leu
                85                  90                  95

Glu Ala Val Glu Ala Thr Phe Trp Ile Ser Ala Phe Ala Arg Leu Arg
            100                 105                 110

Gly Asn Glu Pro Ser Thr Cys Asp Thr Val Met Met Ser Cys Val Ile
        115                 120                 125

Gly Cys Ile Ser Leu Val Cys Gly Ala Met Phe Val Ala Ile Val Ser
    130                 135                 140

Cys Ala Val Lys Ile Ser Arg Ile Val Arg Thr Met Thr Gln Ala His
145                 150                 155                 160

Ala Leu Arg Glu Thr Ile Gln Arg Gln Leu Ala Ala Arg Ala Thr Asp
                165                 170                 175

Met Arg Ser Ala Tyr Ser Lys Leu Lys Gly Ile Ile Ala Ile Arg Ala
            180                 185                 190

Leu Asn Glu Val Glu Arg Gly His Arg Lys Leu Arg Asn Lys Met Ile
        195                 200                 205

Thr Ala Phe Val Ala Asn Ala Leu Ile Thr Leu Ala Phe Cys Ala Leu
    210                 215                 220
```

```
Leu Ala Ser Ala Val Ile Ala Ala Phe Phe Phe Gly Ala Ala Ser Ala
225                 230                 235                 240

Gly Leu Ala Ser Val Phe Phe Gly Cys Leu Trp Gly Gly Ile Gly Ala
                245                 250                 255

Leu Ala Val Gly Val Leu Val Gly Ile Val Ser Gly Ile Cys Gln Arg
            260                 265                 270

Asn Tyr Lys Val Glu Ala Ala Arg Cys Ile Gln Arg Gly Ala Leu Tyr
        275                 280                 285

Ala Leu Val Leu Glu Lys Met Gln Arg Phe Pro Lys Glu Phe Leu Lys
    290                 295                 300

Asp Gly Val Ala Lys Ser Val Val Ala Ile Gln Ala Gly Glu Ser Leu
305                 310                 315                 320

Asp Thr Gly Glu Leu Ala Trp Glu Glu Met Pro Ser Ile Thr Ala Cys
                325                 330                 335

Leu Gly Arg Glu Gly Met Asp Ala Gln Ala Tyr Ser Phe Leu Ser Ala
            340                 345                 350

Ser Pro Leu Asp Ala Arg Ile Glu
        355                 360

<210> SEQ ID NO 4
<211> LENGTH: 159
<212> TYPE: PRT
<213> ORGANISM: Chlamydia muridarum

<400> SEQUENCE: 4

Met Ser Ala Pro Ile Pro Pro Ala Lys Asp Ser Lys Tyr Val Ser Ala
1               5                   10                  15

Leu Pro Pro Leu Glu Pro Leu Arg Thr Pro Pro Met Ala Glu Leu Leu
            20                  25                  30

Phe Gly Ile Tyr Ser Leu Leu Leu Glu Ala Val Glu Ile Arg Gln Gln
        35                  40                  45

Thr Val Leu Thr Gln Ser Gln Gln Leu Asn Asp Asn Thr Asn Ile Gln
    50                  55                  60

Gln Gln Leu Asn Gln Glu Thr Asn Arg Ile Lys Tyr Ala Val Val Asn
65                  70                  75                  80

Ala Gly Ala Lys Glu Asp Glu Ile Thr Arg Val Gln Asn Gln Asn Gln
                85                  90                  95

Asn Tyr Ser Ala Gln Arg Ser Asn Ile Gln Asp Gln Leu Val Thr Ala
            100                 105                 110

Arg Gln Asn Gly Gln Ile Ile Leu Ser His Ala Ser Thr Asn Ile Asn
        115                 120                 125

Ile Met Gln Gln Ile Ala Gln Met Asn Ser Ser Phe Ile Lys Thr Leu
    130                 135                 140

Asn Ser Val Gly Ser Thr Val Asn Gln Leu Asn Lys Pro Leu Ser
145                 150                 155

<210> SEQ ID NO 5
<211> LENGTH: 408
<212> TYPE: PRT
<213> ORGANISM: Chlamydia muridarum

<400> SEQUENCE: 5

Met Met Glu Pro Leu Arg Phe Gly Tyr Phe Phe Cys Ile Leu Phe Ile
1               5                   10                  15

Gly Leu Leu Gln Thr Val Phe Ala Lys Glu Pro Asp Ser Cys Pro Asp
            20                  25                  30
```

Cys Lys Asn Asn Trp Lys Glu Val Thr His Thr Asp Gln Leu Pro Glu
             35                  40                  45

Asn Ile Ile His Ala Asp Asp Ala Cys Tyr His Ser Gly Tyr Val Gln
 50                  55                  60

Ala Leu Ile Asp Met His Phe Leu Asp Ser Cys Cys Gln Val Ile Val
 65                  70                  75                  80

Glu Asp Gln Thr Ala Tyr Leu Phe Ser Leu Pro Gln Asp Asp Val Thr
                 85                  90                  95

Arg Asn Ala Ile Ile Asn Leu Ile Lys Asp Leu Pro Phe Ile Gln Ser
                100                 105                 110

Val Glu Ile Cys Gln Ala Ser Tyr Gln Thr Cys His His Gln Gly Pro
            115                 120                 125

Tyr Gly Lys Ser Ser Leu Pro Glu Gln Arg Ser Phe Cys Thr Lys Val
            130                 135                 140

Cys Gly Lys Glu Ala Ile Trp Leu Pro Gln Asn Thr Ile Leu Phe Thr
145                 150                 155                 160

Pro Leu Val Ala Asp Pro Arg Gln Ala Thr Asn Ser Ala Gly Ile Arg
                165                 170                 175

Phe Asn Asp Glu Val Ile Gly Lys Arg Val Gly Ser Ala Val Phe Gly
                180                 185                 190

Gly Asp Phe Ile Phe Leu Arg Leu Phe Asp Val Ser Arg Phe His Gly
            195                 200                 205

Asp Met Asp Ile Gly Leu Gln Gly Ala Val Phe Ser Val Phe Asp Leu
            210                 215                 220

Asp Asn Pro Asp Ala Cys Met Val Asn Ser Asp Phe Phe Val Ser Ala
225                 230                 235                 240

Leu Leu Ser Phe Ala Val Asn Lys Trp Ser Tyr Arg Leu Arg Leu Trp
                245                 250                 255

His Leu Ser Ser His Leu Gly Asp Glu Phe Ile Leu Ala Asn Gln Leu
                260                 265                 270

Pro Pro Gly Lys Arg Tyr Asn Arg Ser Asp Glu Ala Val Asp Phe Phe
            275                 280                 285

Ala Ser Phe Arg Tyr Thr Pro Gln Ile Arg Val Tyr Gly Gly Ile Gly
            290                 295                 300

Tyr Ile Ile Ser Arg Asp Leu Thr Phe Pro Glu Asp Pro Leu Tyr Phe
305                 310                 315                 320

Glu Gly Gly Leu Glu Leu Arg Pro Phe Gly Leu Arg Glu Asp Asn Leu
                325                 330                 335

His Ala Gln Pro Ile Phe Ala Met His Phe Arg Phe Trp Gly Glu His
                340                 345                 350

Asp Phe Ser Ile Asp Gln Thr Tyr Ile Leu Gly Met Glu Trp Ser Lys
            355                 360                 365

Phe Gln Asp Val Gly Arg Lys Ile Arg Ala Val Leu Glu Tyr His Gln
            370                 375                 380

Gly Phe Ser His Glu Gly Gln Phe Val Arg Glu Cys Asp Tyr Tyr
385                 390                 395                 400

Gly Phe Arg Leu Ser Tyr Gly Phe
                405

<210> SEQ ID NO 6
<211> LENGTH: 365
<212> TYPE: PRT
<213> ORGANISM: Chlamydia muridarum

<400> SEQUENCE: 6

```
Met Val Ser Phe Asp Leu Ser Val Thr Thr Asn Ile Gly Ala Gly
 1               5                  10                  15

Tyr Asp Asp Ile Gln Arg Met Leu Asn Gly Val Thr Cys Ser Ser Gly
            20                  25                  30

Gly Met Gly Leu Leu Thr Pro Ser Ala Cys Ser Pro Met Ser Ser Phe
        35                  40                  45

Cys Ser Ser Asn Gln Pro Tyr Ser Ala Arg Asp Leu Lys Asn Arg Ile
        50                  55                  60

His Gln Phe Cys Gln His Ser Gly Pro Ile Thr Gly Phe Tyr Ser Leu
 65                  70                  75                  80

Tyr Asn Glu Lys Ile Met Phe Glu Glu Ala Leu Leu Val Pro Thr Val
                85                  90                  95

Leu Glu Ala Val Glu Ser Thr Phe Trp Ile Ser Ala Leu Ser Arg Leu
            100                 105                 110

Gly Gly Glu Arg Pro Ser Thr Phe Asp Thr Val Ile Leu Ser Phe Phe
        115                 120                 125

Val Gly Leu Ile Ser Leu Val Cys Gly Ala Met Phe Val Gly Ile Val
        130                 135                 140

Ser Ser Ala Val Lys Ile Tyr Arg Leu Met Gln Thr Met Arg Gln Ala
145                 150                 155                 160

Arg Thr Leu Asn Glu Asn Val Gln Arg Leu Leu Ala Pro Gln Ala Thr
                165                 170                 175

Asn Met Arg Ser Ala Phe Ala Lys Leu Lys Gly Ile Val Ala Ser Lys
            180                 185                 190

Ala Leu Asp Gln Val Glu Gln Gly Tyr Arg Lys Phe Arg Asn Arg Met
        195                 200                 205

Ile Thr Ser Phe Val Ala Asn Ala Leu Ile Thr Ile Ala Phe Cys Ala
        210                 215                 220

Leu Leu Ala Ser Val Ile Leu Ser Ala Phe Phe Ile Gly Gly Ala Ser
225                 230                 235                 240

Gly Cys Leu Met Ala Ala Phe Phe Gly Cys Leu Gly Val Gly Leu Gly
                245                 250                 255

Ser Leu Thr Ile Gly Met Leu Val Gly Ile Val Ser Ala Ile Cys Gln
            260                 265                 270

Arg Lys His Lys Gln Glu Ala Ala Arg Cys Ile Gln Arg Gly Ile Phe
        275                 280                 285

Tyr Ser Leu Ile Leu Glu Gln Met Gln Arg Phe Pro Lys Asp Phe Phe
        290                 295                 300

Arg Asp Pro Val Ala Lys Ser Ile Met Ala Ile Gln Ala Gly Glu Ala
305                 310                 315                 320

Leu Asp Glu Gly Lys Leu Ser Trp Lys Glu Met Pro Ser Ile Thr Ala
                325                 330                 335

Cys Leu Gly Arg Glu Gly Leu Asp Ala Gln Ala Tyr Ser Phe Ile Ser
            340                 345                 350

Ser Ser Pro Leu Asp Gly Arg Ile Glu Glu Ala Phe Arg
        355                 360                 365
```